US008642327B2

(12) United States Patent
Liu et al.

(10) Patent No.: US 8,642,327 B2
(45) Date of Patent: Feb. 4, 2014

(54) VECTOR FOR INHIBITION-BASED HIGH-THROUGHPUT SCREEN STRATEGY

(75) Inventors: Wei-Kuang Liu, Taipei (TW); Min-Pey Ding, Taipei County (TW)

(73) Assignee: Scinopharm Taiwan, Ltd., Tainan County (TW)

(*) Notice: Subject to any disclaimer, the term of this patent is extended or adjusted under 35 U.S.C. 154(b) by 164 days.

(21) Appl. No.: 13/231,436

(22) Filed: Sep. 13, 2011

(65) Prior Publication Data

US 2012/0070891 A1    Mar. 22, 2012

Related U.S. Application Data

(62) Division of application No. 12/792,924, filed on Jun. 3, 2010.

(60) Provisional application No. 61/213,459, filed on Jun. 11, 2009.

(51) Int. Cl.
*C12N 15/00* (2006.01)

(52) U.S. Cl.
USPC ...................................................... 435/320.1

(58) Field of Classification Search
USPC ...................................................... 435/320.1
See application file for complete search history.

(56) References Cited

U.S. PATENT DOCUMENTS

| | | | | |
|---|---|---|---|---|
| 5,837,464 | A * | 11/1998 | Capon et al. | 435/5 |
| 7,786,344 | B2 * | 8/2010 | Kock et al. | 800/278 |
| 2005/0266552 | A1 * | 12/2005 | Doench et al. | 435/358 |
| 2007/0044164 | A1 * | 2/2007 | Dickins et al. | 800/14 |
| 2009/0148936 | A1 * | 6/2009 | Stout et al. | 435/320.1 |
| 2009/0217399 | A1 * | 8/2009 | Stern et al. | 800/13 |

OTHER PUBLICATIONS

Ngoi et al. Current Gene Therapy (2004), 4:15-31.*
Lewin et al. BMC Biotech. (2005), 5:19, 1-9.*

* cited by examiner

*Primary Examiner* — Jon E Angell
(74) *Attorney, Agent, or Firm* — Andrews Kurth LLP; Michael Ye

(57) ABSTRACT

A method for screening cells with high level expression of a target protein is disclosed. The method includes introducing into a plurality of host cells a DNA construct that encodes both a target protein and an inhibitor to an endogenous selectable marker in the host cells, screening host cells harboring the DNA construct for the expression of the endogenous selectable marker, and isolating cells with reduced expression of the selectable marker. Also disclosed is a DNA construct configured to express both the target protein and the inhibitor inside the host cell.

10 Claims, 14 Drawing Sheets

C

D

VECTOR FOR INHIBITION-BASED HIGH-THROUGHPUT SCREEN STRATEGY

RELATED APPLICATIONS

This application is a divisional application of U.S. Ser. No. 12/792,924, filed Jun. 3, 2010 which claims the priority of U.S. Provisional Application No. 61/213,459, filed on Jun. 11, 2009. Both of which are incorporated herein by reference in their entirety.

TECHNICAL FIELD

The disclosed technology generally relates to biotechnology and molecular biology and, in particular, to high-throughput screening of cell clones.

BACKGROUND

A key step in the generation of cell lines producing recombinant proteins is the selection of viable clones following the incorporation of the gene of interest into the host cell. For industrial-scale bio-production, a clone in which the product gene is stably integrated and yields a high level of the protein product is highly desired.

In a heterogeneous population, the integration of a recombinant gene into the host genome is a largely random event. The proportion of cells containing multiple copies of stably integrated genes would be small compared to those with low copy numbers. The high-producing subclones are rare and tend to be diluted out by the faster growing non- or low-producing cells. Thus, to isolate a subclone with an increased production rate, many wells would need to be screened and tested. In general, limited dilution methods are tedious and time consuming.

The advent of selection methods that use flow cytometry and cell sorting considerably increased the number of cells that can be screened. Several million cells can be screened in a short time, and subpopulations and single cells can be isolated from within mixed-cell populations even when they are present at frequencies as low as $10^{-6}$ within the population.

Flow cytometry was partnered with a non-fluorescent reporter protein for rapid, early stage identification of clones producing high levels of a target protein. This has been facilitated by the availability of antibody and ligand-conjugated fluorochromes enabling isolation of cells based on cell-surface protein expression. For example, a cell surface protein, not normally expressed on host cells, may be co-expressed, with the target protein as a reporter.

In the absence of a correlation between surface expression and productivity, cells can be isolated based on levels of intracellular proteins using reporter molecules such as green fluorescent protein (GFP). The GFP has become an important reporter for gene expression and the selection of cells based on inducible gene products. In mammalian cell lines, GFP has been used for the selection of high-producing clones by co-expression with recombinant proteins and selection based on fluorescence intensity. A correlation between GFP fluorescence intensity and recombinant protein production has been seen for several cell lines expressing various recombinant proteins. However, expression of these selection markers increases the load on the protein expression machinery in the cells and reduces the production of the target protein.

SUMMARY

One aspect of the present invention relates to a method for screening cells with high level expression of a target protein. The method includes introducing into a plurality of host cells a DNA construct that encodes both a target protein and an inhibitor to an endogenous selectable marker in the host cells, screening host cells harboring the DNA construct for the expression of the endogenous selectable marker, and isolating cells with reduced expression of the selectable marker. The DNA construct is configured to express both the target protein and the inhibitor inside the host cell.

In an embodiment, the inhibitor is selected from the group consisting of small interfering RNA (siRNA), small hairpin RNA (shRNA), microRNA (miRNA), hybrid of miRNA and shRNA, and antisense RNA.

In another embodiment, the inhibitor is a shRNA.

In another embodiment, the endogenous selectable marker is a fluorescent marker and the isolating step comprises sorting cells with a fluorescence activated cell sorter (FACS).

In another embodiment, the DNA construct further encodes a dihydroforate reductase (DHFR) and the host cells are DHFR-deficient cells.

Another aspect of the present invention relates to a high throughput screening method for selecting transgene expressing cells. The method includes transfecting host cells that express a fluorescent protein with a vector carrying at least one transgene and an interfering RNA that inhibits the expression of the fluorescent protein; measuring fluorescence intensity in the transfected cells; and isolating cells having a fluorescence intensity that is lower than the fluorescence intensity of untransfected cells.

In one embodiment, the fluorescent protein is green fluorescent protein (GFP).

In another embodiment, the interfering RNA is a mir-30-based shRNA.

In another embodiment, the isolating step comprises sorting cells with a FACS.

In another embodiment, the cells that express a fluorescent protein are DHFR-deficient CHO cells.

In another embodiment, the at least one transgene is linked to a gene encoding DHFR by an internal ribosome entry site (IRES).

Another aspect of the present invention relates to an expression vector for high-throughput screening of cells harboring the expression vector. The expression vector comprises a first nucleotide sequence encoding a target protein, a second nucleotide sequence encoding an exogenous selection marker for a host cell, a third nucleotide sequence encoding an inhibitor to an endogenous selection marker in the host cell, and one or more regulatory elements that control the expression of the first, second and third nucleotide sequences in the host cell. The first nucleotide sequence is linked to the second nucleotide sequence by an internal ribosome entry site (IRES).

In an embodiment, the expression vector further comprises one or more anti-repressor elements.

In a related embodiment, the one or more anti-repressor elements includes a partial mouse anti-repressor element 40.

In another embodiment, the inhibitor is an interfering RNA.

In a related embodiment, the interfering RNA is a miR-30-based shRNA.

In another embodiment, the endogenous selection marker is a fluorescent protein.

In a related embodiment, the fluorescent protein is green fluorescent protein.

In another embodiment, the exogenous selectable marker is dihydroforate reductase.

In another embodiment, the one or more regulatory elements include a CMV IE enhancer.

DETAILED DESCRIPTION

Figure 1:
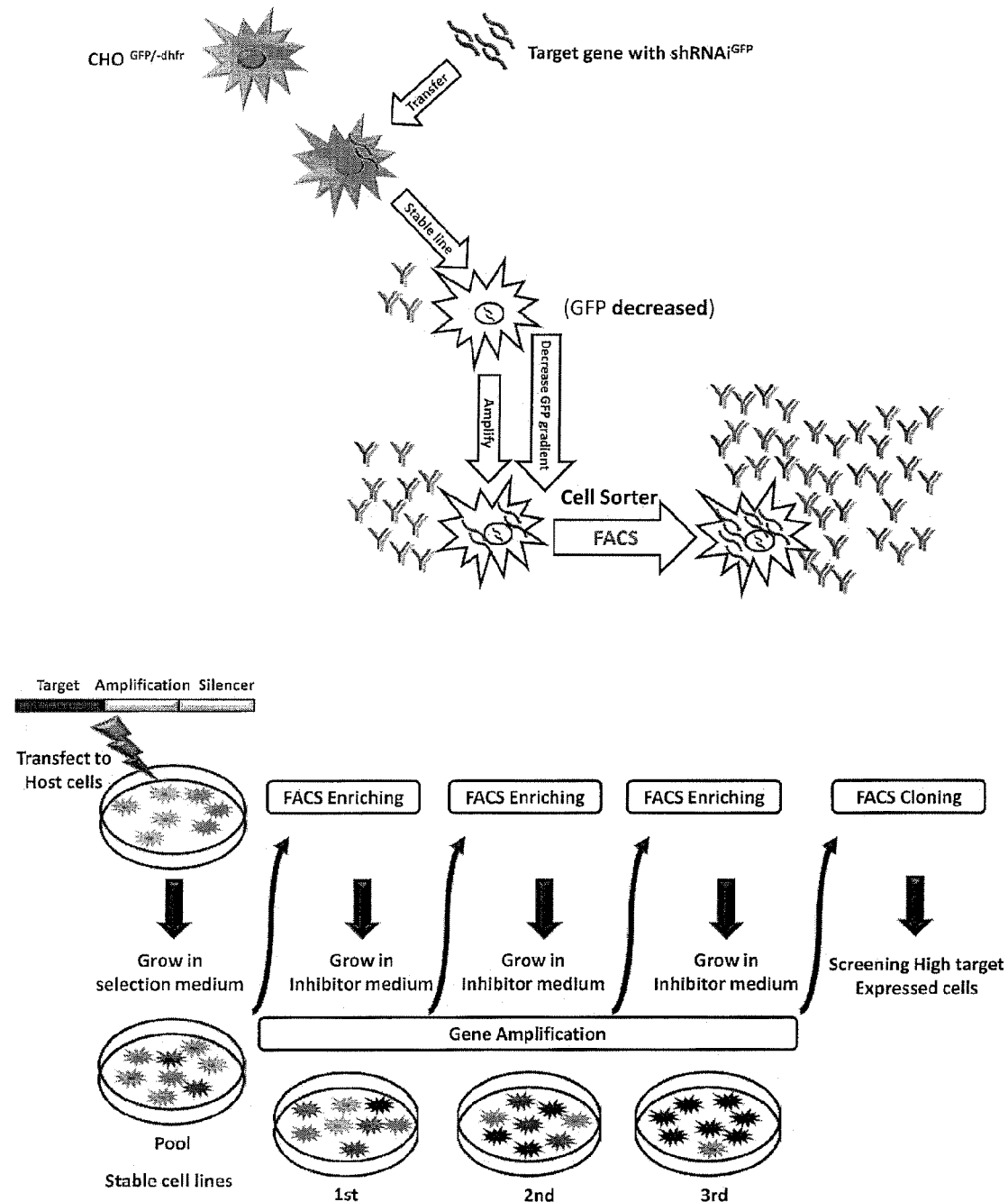
FIG. 1 is a diagram showing a GFP-based screening strategy for high transgene expression cell clones.

A method for screening cells with high level expression of an exogenous protein is disclosed. In one embodiment, the method includes the steps of introducing into a plurality of host cells a DNA construct that encodes both a target protein and an inhibitor to an endogenous selectable marker in the host cells, wherein the construct is configured to express both the target protein and the inhibitor inside the host cell; screening host cells harboring the DNA construct for the expression of the endogenous selectable marker, and isolating cells with reduced expression of the endogenous selectable marker.

As used hereinafter, the terms "cell"/"host cell" and "cell line"/"host cell line" are respectively typically defined as a eukaryotic cell and homogeneous populations thereof that are maintained in cell culture by methods known in the art, and that have the ability to express heterologous proteins. In one embodiment, the cells are CHO cells. In another embodiment, the cells are CHO cells that express GFP as an endogenous selection marker. In another embodiment, the cells are CHO cells that are deficient in DHFR gene and express GFP as an endogenous selection marker.

As used hereinafter, the term "expression" is typically used to refer to the production of a specific RNA product or products, or a specific protein or proteins, in a cell. In the case of RNA products, it refers to the process of transcription. In the case of protein products, it refers to the processes of transcription, translation and optionally post-translational modifications. In the case of secreted proteins, it refers to the processes of transcription, translation, and optionally post-translational modification (e.g., glycosylation, disulfide bond formation, etc.), followed by secretion. In the case of multimeric proteins, it includes assembly of the multimeric structure from the polypeptide monomers. The corresponding verbs of the noun "expression" have an analogous meaning as the noun.

As used hereinafter, the term "selectable marker" is typically used to refer to a gene and/or protein whose presence can be detected directly or indirectly in a cell, for example, a gene and/or a protein that inactivates a selection agent and protects the host cell from the agent's lethal or growth-inhibitory effects (e.g., an antibiotic resistance gene and/or protein). Another possibility is that the selection marker induces fluorescence or a color deposit (e.g., green fluorescent protein and derivatives, luciferase, or alkaline phosphatase). The term "endogenous selectable marker" refers to a selectable marker that is encoded by a polynucleotide that is present in the host cell prior to the introduction of the DNA construct into the host cell. The coding sequence for the "endogenous selectable marker" may exist in either integrated form (i.e., integrated into the cell genome) or in episomal form.

As used hereinafter, the term "DNA construct" refers to an expression or transformation construct. The DNA construct comprises at least one expression unit or expression cassette. The term "expression unit or expression cassette" is herein defined as a unit capable of expressing a coding sequence or an open reading frame. An "expression unit or expression cassette" typically comprises one or more regulatory elements operably linked to a transgene that encodes a molecule of interest (i.e., a polypeptide or a polynucleotide).

A "regulatory element" is a nucleic acid sequence that regulates the expression of a transgene by being operably linked to the coding sequence. Examples of regulatory sequences include, but are not limited to, appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. A regulatory sequence may act in cis or trans configuration, or at a distance to control a gene of interest.

A "transgene" is a nucleic acid sequence that is to be delivered or transferred to a mammalian cell. A transgene may encode a protein, peptide or polypeptide that is useful as a marker, reporter or therapeutic molecule. A transgene may also encode a protein, polypeptide or peptide that is useful for protein production, diagnostic assays or for any transient or stable gene transfer in vitro or in vivo. Alternatively, a transgene may encode a functional polynucleotide, such as miRNA, RNAi, shRNA, antisense RNAs, ribozyme or other regulatory nucleic acids. Transgenes also include DNA sequences that are used to induce DNA recombination and gene repair.

A nucleic acid sequence is "operably linked" to another nucleic acid sequence when the former is placed into a functional relationship with the latter. For example, a DNA for a presequence or secretory leader peptide is operably linked to DNA for a polypeptide if it is expressed as a preprotein that participates in the secretion of the hepolypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, synthetic oligonucleotide adaptors or linkers are used in accordance with conventional practice.

The "inhibitor to a selectable marker" can be a polypeptide or a polynucleotide that inhibits, directly or indirectly, the expression or activity of the selectable marker. In one embodiment, the inhibitor is a polynucleotide, such as a small interfering RNA (siRNA), a small hairpin RNA (shRNA), a microRNA (miRNA), a hybrid of miRNA and shRNA, or an antisense RNA molecule that inhibits the expression of the selectable marker in the host cell. In another embodiment, the inhibitor is a polypeptide, such as transcription regulator, that inhibits the expression of the selectable marker in the host cell. In yet another embodiment, the inhibitor is a polypeptide, such as an antibody, that inhibits a biological activity of the selectable marker.

As used herein, the term "siRNA" refers to an RNA agent, preferably a double-stranded agent, of about 10-50 nucleotides in length (the term "nucleotides" including nucleotide analogs), preferably between about 15-25 nucleotides in length, more preferably about 17, 18, 19, 20, 21, 22, 23, 24, or 25 nucleotides in length, the strands optionally having overhanging ends comprising, for example, 1, 2 or 3 overhanging nucleotides (or nucleotide analogs), which is capable of directing or mediating RNA interference. Naturally-occurring siRNAs are generated from longer dsRNA molecules (e.g., >25 nucleotides in length) by a cell's RNA interference (RNAi) machinery.

The term "RNA interference" or "RNAi", as used herein, refers generally to a sequence-specific or selective process by which a target molecule (e.g., a target gene, protein or RNA) is downregulated. In specific embodiments, the process of "RNA interference" or "RNAi" features degradation of RNA molecules, e.g., RNA molecules within a cell, said degradation being triggered by an RNA agent. Degradation is catalyzed by an enzymatic, RNA-induced silencing complex (RISC). RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by introducing small interfering RNA molecules into a cell to silence the expression of target genes.

As used hereinafter, the term "shRNA", refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The shRNA hairpin structure is cleaved by the cellular machinery into siRNA, which is then bound to the RNA-induced silencing complex (RISC). This complex binds to and cleaves mRNAs which match the siRNA that is bound to it.

The DNA construct may further contain plasmid elements for replication and selection in bacteria during the construction of the DNA construct. The DNA construct may also contain other selection markers to facilitate the amplification of the DNA construct in the host cell. Selection marker(s) encoded by the DNA construct are considered exogenous selection markers. Examples of exogenous selection markers include, but are not limited to, resistance to antibiotics (e.g. neomycin gene encoding resistance to G418) or enzyme analogs (e.g. dihydrofolate reductase gene encoding methotrexate resistance).

In one embodiment, the DNA construct contains a bicistronic expression cassette in which the open reading frame for the protein of interest is linked to the coding sequence of the exogenous selection marker or the inhibitor of the endogenous marker by an internal ribosome entry site (IRES), so that they are transcribed in the same mRNA but are translated independently. Since they each arise from a common mRNA, the exogenous selection marker's or the inhibitor's expression level accurately predicts the relative expression level of the protein of interest for each clone. Preferably, the open reading frame for the protein of interest in the bicistronic expression cassette is located upstream of the coding sequence of the exogenous selection marker or the inhibitor of the endogenous selectable marker.

For example, to improve the accuracy and throughput of multiple rounds of methotrexate (MTX) amplification, the gene encoding a therapeutic protein (such as the light chain of an antibody) is linked to an exogenous selectable marker (such as DHFR) at the 3'-end by an IRES, so that they are transcribed in the same mRNA but are translated independently. The lower efficiency of IRES-mediated translation relative to 5' cap-mediated translation ensures that cellular resources are utilized mainly for production of the therapeutic protein rather than the DHFR protein. However, since they arise from the same mRNA, the DHFR amplification level accurately predicts, for each clone, the relative expression level of the therapeutic protein.

In another embodiment, the DNA construct further contains one or more anti-repressor element (ARE) that counteract chromatin associated repression. As used hereinafter, an ARE (or anti-repressor sequence, which is used interchangeably herein) is a naturally occurring DNA element isolated from eukaryotic genomes on the basis of its ability to block transgene repression. An ARE comprises the capacity to influence transcription of genes in cis and/or provide a stabilizing and/or an enhancing effect. It has been demonstrated that when AREs flank transgenes, the transgene expression level of randomly selected recombinant cell lines can be increased to levels approaching the maximum potential expression of the transgene's promoter. Moreover, the expression level of the transgene is stable over many cell generations, and does not manifest stochastic silencing. Therefore, ARE confers a degree of position-independent expression on transgenes that is not possible with conventional transgenic systems. The position independence means that transgenes that are integrated in genomic locations that would result in transgene silencing are, with the protection of ARE, maintained in a transcriptionally active state. In one embodiment, the ARE is a partial mouse ARE40 fragment. In another embodiment, the DNA construct contains multiple partial mouse ARE40 fragments.

Methods for introducing the DNA construct into the cell are well know in the art. Examples of such methods include, but are not limited to, electroporation, lipofection, calcium phosphate or calcium chloride co-precipitation and DEAE-dextran-mediated transfection. The DNA construct may also be introduced into the cells by a virus vector. Commonly used virus vectors include, but are not limited to, adenovirus vectors, adeno-associated virus (AAV) vectors, herpes virus vectors and retrovirus vectors.

Cells transfected with the DNA construct are screened for both the expression of the exogenous and endogenous selectable markers. High level expression of the selectable marker inhibitor from the DNA construct would result in reduced expression and/or activity of the endogenous selectable marker. Cells with reduced expression of the selectable marker are then isolated and subcloned to determine the level and stability of transgene expression.

In certain embodiments, the endogenous selectable marker is a protein that can be induced to emit fluorescence. In these embodiments, the screening step and the isolating step can be performed simultaneously using a fluorescence activated cell sorter (FACS).

In other embodiments, cells transfected with the DNA construct are first subjected to one or more rounds of selection with the exogenous marker (e.g., selection of G418 resistant and/or methotrexate resistant clones). The selected cells are then screened for reduced expression and/or activity of the endogenous selectable marker.

Also disclosed is a DNA construct configured to allow high-throughput screening of cells harboring the DNA construct. In one embodiment, the DNA construct contains coding sequences for a target protein and coding sequences for an inhibitor to an endogenous selectable marker in a host cell, wherein the DNA construct is configured to express both the target protein and the inhibitor inside the host cell.

In one embodiment, the inhibitor is a small interfering RNA (siRNA), a small hairpin RNA (shRNA), a microRNA (miRNA), a hybrid of miRNA and shRNA, or an antisense RNA molecule that inhibits the expression of the endogenous selectable marker in the host cell.

In another embodiment, the inhibitor is a polypeptide, such as transcription regulator, that inhibits the expression of the endogenous selectable marker in the host cell.

In another embodiment, the inhibitor is a polypeptide, such as an antibody, that inhibits a biological activity of the endogenous selectable marker.

In another embodiment, the endogenous selectable marker is a protein that induces fluorescence.

In another embodiment, the DNA construct further comprises one or more anti-repressor elements.

The technology described in the present invention enables rapid identification and isolation of high production clones from a heterogeneous population of transfected cells, decreasing the labor and time associated with standard limiting dilution cloning methods. In addition, because this technology can identify desired cells that are rare events in the population, it can shorten the development timeline by reducing the number of rounds of pool amplification prior to isolating the high producing clones or by first isolating the high producing clones for drug amplification and subcloning.

EXAMPLES

The ease and efficiency of green fluorescent protein (GFP)/fluorescence activated cell sorter (FACS)-based screening methods had been demonstrated in previous studies. In these previous reports, GFP was incorporated as part of a fusion protein or part of a bicistronic construct using either an internal ribosomal entry site (IRES) or a two promoter system. Cells with a high-level of GFP correlated with a high level of the protein product of interest. This can be attributed to the stable integration of a high number of copies of the recombinant gene or that the gene had been integrated into sites of very high transcriptional activity. Although these methods have been shown to be effective, there may be some concern regarding the use of GFP-containing cell lines for the production of human therapeutics. Furthermore, it appears unnecessary to burden the cell's metabolic machinery with GFP production after the subpopulation has been isolated. This cellular resource could potentially be diverted to increasing cell growth or recombinant protein production. The following examples describe a novel technique for selecting high-producing cell clones that reversely uses GFP as a selection marker, coupled with sorting through FACS.

FIG. 1 is a schematic showing the GFP-based selection process. Briefly, plasmid vectors containing the cDNA encoding for GFP are transfected into DHFR-deficient CHO cells. Cells that have successfully acquired the desired vector are fluorescent. The GFP-expression cell is set as the parental host cell for recombinant-protein expression.

For desired recombinant-protein production, the parental host cells are transfected with the shRNAmir$^{eGFP}$-containing vector, and then FACS sorted to screen for cells with low fluorescent intensity. Cell cultures after several rounds of increasing MTX challenge were subjected to repeated rounds of sorting and expansion. Cell clones with the lowest GFP fluorescence intensity would correspond to the clones with the highest transgene expression. Finally, the selected clones are expanded and tested for production and stability. As FACS enables a large number of cells to be easily screened, the chance of obtaining high producing clones would be greatly increased compared to limited dilution methods. Moreover, the procedure is less labor-intensive and may significantly reduce the time required to generate clones for bio-production.

Example 1

Establishment of CHO$^{+GFP/-dhfr}$ Cell Line

The Chinese Hamster Ovary dihydrofolate reductase deficient cell line (CHO/$^{dhfr-}$) was maintained in Iscove's modified Dulbecco's medium (IMDM, Gibco, Cat. No. 12200) supplemented with HT (0.1 mM sodium hypoxanthine and 0.016 mM thymidine, Gibco, Cat No. 11067), 10% FBS (Biological Industries, Cat. 04-001-1A) and 2 µM Methothrexate Hydrate (MTX, Sigma, SI-M8407).

The CHO/$^{dhfr-}$ cells were transfected with 5 ug of plasmid vector containing the cDNA encoding for GFP (pFLAg-eGFP-IRES-Puro,) with lipofectamine according to the instructions from Lipofectamine™ Invitrogen Puls™ Reagent (Cat. No. 11514-015). Transfected cells were selected using 5 µg/ml of puromycin dihydrochloride (Sigma, SI-P8833). After 10 days of selection in IMDM medium supplemented with HT, 10% FBS, 2 µM MTX and selective antibiotics, cells were maintained in above medium. The GFP-expressing CHO$^{-dhfr}$ cell (CHO$^{+GFP/-dhfr}$ cell) is cloned and set as the parental host for recombinant-protein expression.

Example 2

Construction of Expression Vectors (1) The pScinoDP-DHFR Vector

The pScinoDP-DHFR plasmid was constructed by substituting the EGFP gene in the pEGFP-N1 (Clontech) plasmid backbone with an IRES-DHFR fused gene, and inserting an addition SV40 polyA tail and CMV-IE promoter into the pEGFP-N1 (Clontech) plasmid backbone. Briefly, polyA tail and CMV-IE promoter sequence were obtained by PCR amplification using pCEP4 plasmid (Invitrogen) as the template. A fused polyA tail-promoter fused sequence SV40polA-CMV-IE (about 1.2 kb) was created through overlap extension by PCR(OL-PCR). The fused sequence was digested with XhoI/BglII and inserted into XhoI/BglII digested pEGFP-N1 vector. The resulting construct was named pScinoDP.

IRES sequence and DHFR gene were obtained by PCR amplification using pIRES2-EGFP and pSV2-DHFR plasmids as template. A hybrid IRES sequence fragment and DHFR gene fragment (IRES2-DHFR) was produced through overlap extension by PCR (OL-PCR). The hybrid fragment (~1.1 kb) was digested with AgeI/NotI and inserted into AgeI/NotI digested pEGFP-N1 to substitute the EGFP gene in the pEGFP-N1 vector. The resulting construct was named pIRES2-DHFR. A site-directed mutagenesis was performed to eliminate the ApaLI site in the IRES sequence.

Figure 2:
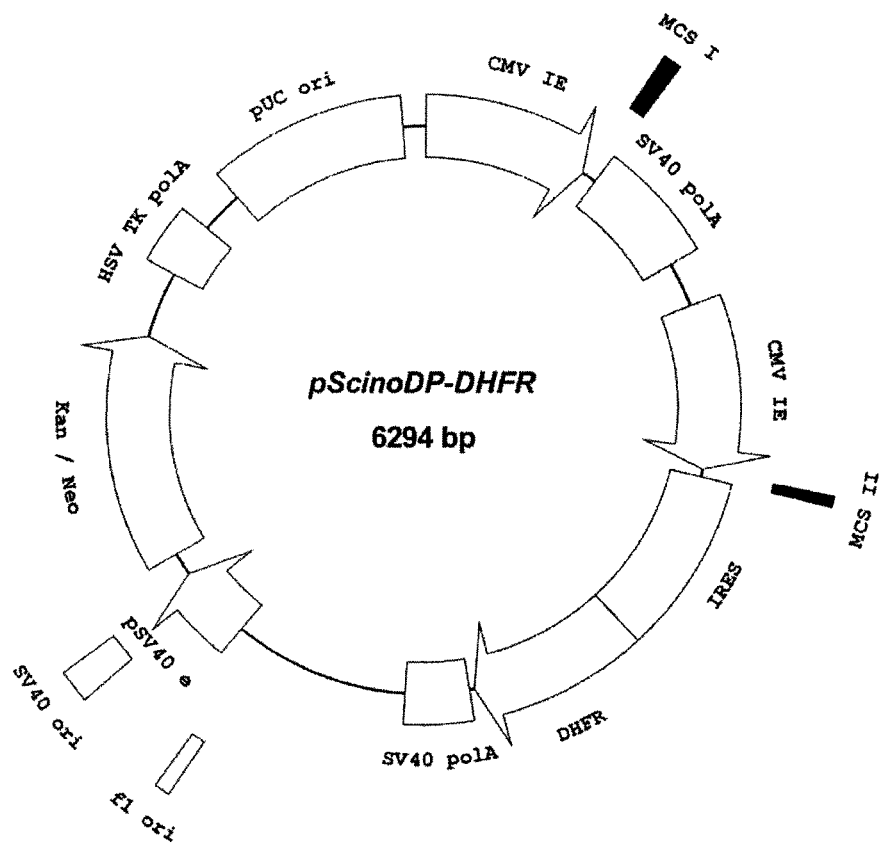
FIG. 2 is a map of expression vector pScinoDP-DHFR.

Plasmid pIRES2-DHFR, with mutated restricted enzyme ApaLI site in IRES sequence, was digested with AgeI/NotI and a 1.2 kb fragment containing IRES sequence and the entire DHFR coding region gene was ligated into AgeI/NotI-digested pScinoDP, generating pScinoDP-DHFR (FIG. 2). All constructs were confirmed by restriction analyses and/or by nucleotide sequencing.

(2) The pScinoDP3-DHFR Vector

Figure 3:
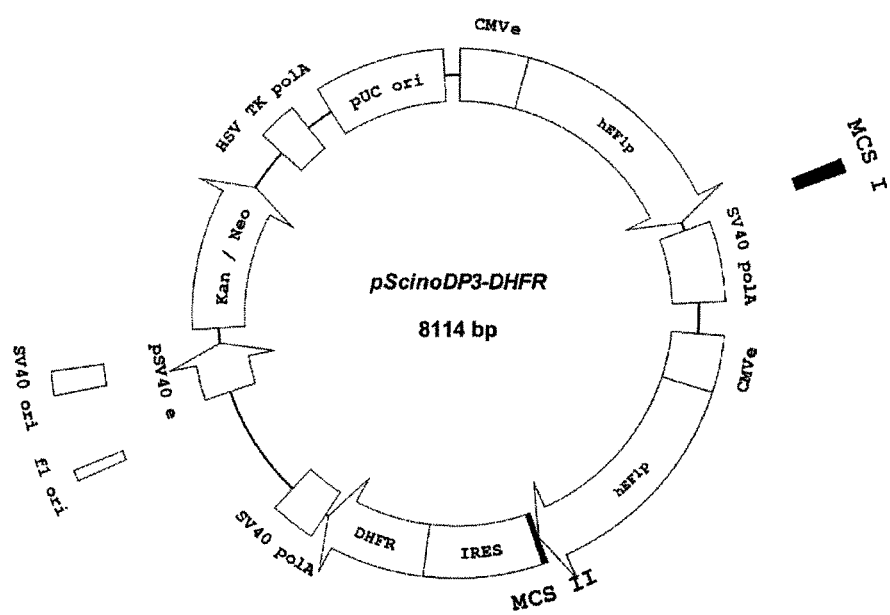
FIG. 3 is a map of expression vector pScinoDP3-DHFR.

The pScinoDP3-DHFR vector is a pScinoDP-DHFR based vector that carries a hEF1α promoter with the CMV-IE enhancer. Briefly, the hEF1α promoter was amplified from pBudCE4.1 vector (Invitrogen). Hybrid CMV-IE enhancer sequence with hEF1α promoter was obtained through subcloning hEF1α promoter after the CMV-IE enhancer on pEGFP-N1 to form pCMVe-hEF1α-EGFP vector. The CMV$^e$-hEF1α fragment was PCR amplified from the pCMV$^e$-hEF1α-EGFP vector and used to replace both CMV promoters in the pScionDP-DHFR vector. The resulting vector is named pScinoDP3-DHFR (FIG. 3).

(3) The pScinoDP3mir-DHFR Vector

The single strand 97nt "mir30-like" shRNAi$^{GFP}$ oligo was generated using PCR as described using the following synthesis skeleton DNA and primers:

```
Single strand 97nt "shRNAi^GFP" DNA oligo
                                     (SEQ ID NO: 1)
5'-TGCTGTTGACAGTGAGCGAGCACAAGCTGGAGTACAACTATAGTGA

AGCCACAGATGTATAGTTGTACTCCAGCTTGTGCCTGCCTACTGCCTCGG

A-3'
```

The underlined, italicized sequences represent the flanking mir30 sequences and the non-underlined, italicized sequence represents the mir30 loop structure. The sample sense and antisense-selected target sequences are shown in bold and underlined bold, respectively. The mir30-like shRNAi$^{GFP}$ is synthesized as a single stranded DNA oligonucleotide with common ends corresponding to part of the endogenous mir30 miRNA flanking sequence.

```
mirFWD-AgeI primer sequence (40 mers):
                                     (SEQ ID NO: 2)
5'-CAGAAGGACCGGTAAGGTATATTGCTGTTGACAGTGAGCG-3' mirREV-HindIII primer sequence (37 mers):
                                     (SEQ ID NO: 3)
5'-CTAAAGTAGCCCCTTAAGCTTTCCGAGGCAGTAGGCA-3'
```

The flanking regions, shown in underlined, italicized sequences, are used as universal flanks to prime a reaction, whereby the entire mir30-like shRNAi$^{GFP}$ is amplified to produce a PCR product that can be cloned into the recipient vector.

PCR was performed using Platinum® Pfx DNA Polymerase and the following profile: 95° C. for 3 min, then 95° C. for 30 s, 54° C. for 30 s, and 75° C. for 30 s for a total of 35 cycles. The resulting PCR products (AgeI-shRNAi$^{GFP}$) were cloned into modified pEGFP-N1 vector (AgeI site destroyed, and additional AgeI and EcoRV sites behind Neomycin gene). The resulting construct was named pEGFP-N1-shRNAi$^{GFP}$. These AgeI-shRNAi$^{GFP}$ sequences were also confirmed by DNA sequencing.

Figure 4:
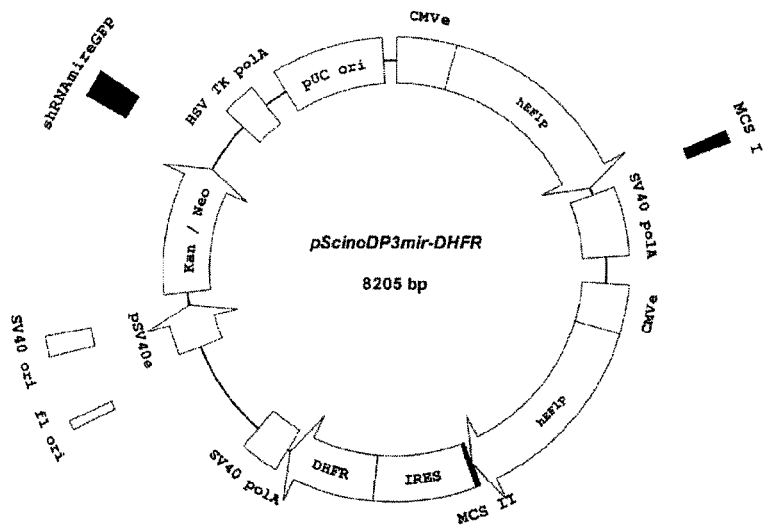
FIG. 4 is a map of expression vector pScinoDP3mir-DHFR.

The pEGFP-N1-shRNAi$^{GFP}$ vector was digested with ApaLI-NotI. The CMV-IE-GFP fragment was replaced with the ScinoDP3-DHFR fragment from pScinoDP3-DHFR. The resulting construct was named pScinoDP3mir-DHFR (FIG. 4).

(4) The pScinoDP8mir-DHFR Vector

The pScinoDP8mir-DHFR vector contains a regulatory DNA element mARE40. Regulatory elements, such as anti-repressing element derived from housekeeping genes, were shown to positively affect specific productivities of recombinant proteins produced from cell lines. Plasmid pEGFP-N1 was used as backbone for this construct. Briefly, the partial mouse anti-repressor element 40 fragment was generated using overlapping-PCR as described using the following synthesis skeleton DNA and primers:

mARE40-L1(+) skeleton DNA:
(SEQ ID NO: 4)
5'-TTGCTCTGAGCCAGCCCACCAGTTTGGAATGACTCCTTTTTATGACTTGAATTTTCA

AGTATAAAGTCTAGTGCTAAATTTAATTTGAACAACTGTATAGTTTTTG-3' mARE40-L1(-) skeleton DNA:
(SEQ ID NO: 5)
5'-TTAGAAATCCTCACACACAACAAGTTTTCATTTCACTTCTAATTCTGAAAAAAACAC

TGCCACCATTTTTTTTCCTTCCCCCAACCAGCAAAAACTATACAGTTGT-3' mARE40-R1(+) skeleton DNA
(SEQ ID NO: 6)
5'-GTGTGTGAGGATTTCTAATGACATGTGGTGGTTGCATACTGAGTGAAGCCGGTGA

GCATTCTGCCATGTCACCCCCTCGTGCTCAGTAATGTACTTTACAGAAATC-3' mARE40-R1(-) skeleton DNA
(SEQ ID NO: 7)
5'-TGGCAGAAATGCAGGCTGAGTGAGACTACCCAGAGAAGAGACCGGATATACACA

AGAAGCATGGTTTATATCAATCTTTTGAGTTTAGGATTTCTGTAAAGTACAT-3' mARE40-5'primer:
(SEQ ID NO: 8)
5'-TTGCTCTGAGCCAGCCCACCAGTTT-3' mARE40-3'AseI primer:
(SEQ ID NO: 9)
5'-GTTATTAATTGGCAGAAATGCAGGCTGAGT-3' mARE40-3'AflII primer:
(SEQ ID NO: 10)
5'-CCCACATGTTGGCAGAAATGCAGGCTGAGT-3' mARE40-3'SpeI primer:
(SEQ ID NO: 11)
5'-GGACTAGTTGGCAGAAATGCAGGCTGAGTG-3'

Figure 5:
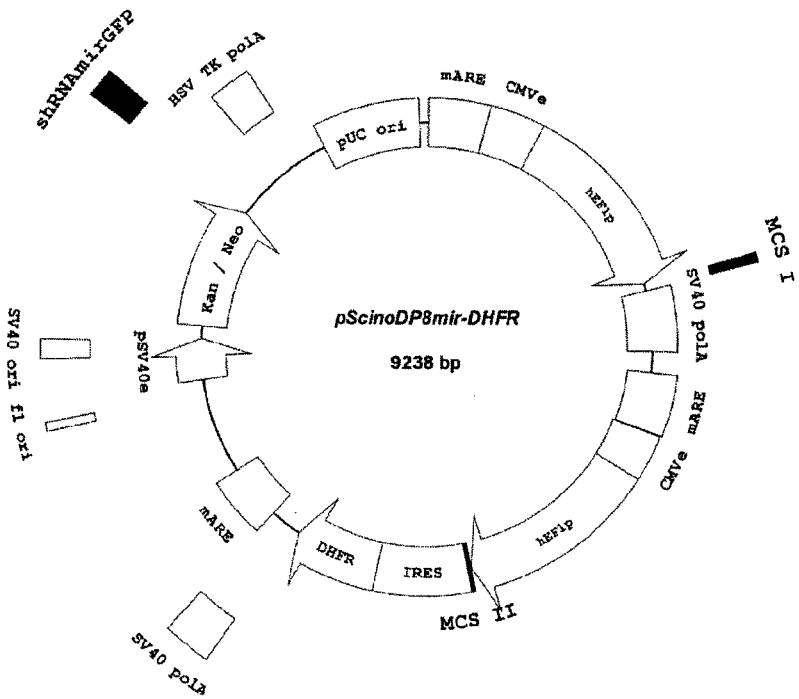
FIG. 5 is a map of expression vector pScinoDP8mir-DHFR.

PCR was performed using Platinum® Pfx DNA Polymerase and the following profile: 95° C. for 3 min, then 95° C. for 30 s, 58° C. for 30 s, and 75° C. for 30 s for a total of 35 cycles. The resulting PCR products (mARE40-AseI and mARE40-AflII) were separately cloned into modified pEGFP-N1(AgeI site destroyed, and additional EcoRV before AseI, and SeaI site before AflII site) vector to form (mARE40-EGFP-N1, and (mARE40-SpeI) were cloned into the pScinoDP3-DHFR (additional EcoRV site before SpeI site) vector to form pScinoDP3-DHFR-F2. The pmARE40-EGFP-N1 vector was digested with AseI-BamHI and the CMV-IE promoter was replaced with the ~1.6 kb AseI-CMV$^e$-hEF1α-BamHI fragment from pScinoDP3-DHFR vector. The resulting construct was named pFmARE40ScinoDP3-EGFP-N1. The pFmARE40ScinoDP3-EGFP-N1 vector was digested with BamHI-NotI and the EGFP gene was replaced with the ~1.6 kb BamHI-SV40polA-mARE40-DP3-IRES-DHFR-NotI fragment from pScinoDP3-DHFR-F2. The resulting construct was named pScinoDP8-DHFR. The pEGFP-N1-shRNAiGFP vector was then digested with ApaLI-NotI and the CMV-IE-GFP fragment was replaced with the ScinoDP8-DHFR fragment from pScinoDP8-DHFR. The resulting construct was named pScinoDP8mir-DHFR (FIG. 5). The complete sequence of the cloned partial mouse anti-repressor element 40 fragment is shown below:

(SEQ ID NO: 12)
5'-TTgCTCTgAgCCAgCCCACCAgTTTggAATgACTCCTTTTTATgACTTgAATTTTCAAgT

ATAAAgTCTAgTgCTAAATTTAATTTgAACAACTgTATAgTTTTTgCTggTTgggggAAggA

AAAAAAATggTggCAgTgTTTTTTTCAgAATTAgAAgTgAAATgAAAACTTgTTgTgTgTgA ggATTTCTAATgACATgTggTggTTgCATACTgAgTgAAgCCggTgAgCATTCTgCCATgTCA

CCCCCTCgTgCTCAgTAATgTACTTTACAgAAATCCTAAACTCAAAAgATTgATATAAA

CCATgCTTCTTgTgTATATCCggTCTCTTCTCTgggTAgTCTCACTCAgCCTgCATTTCTgC

CA-3'.

(5) The pScinoDP9mir-DHFR Vector

Figure 6:
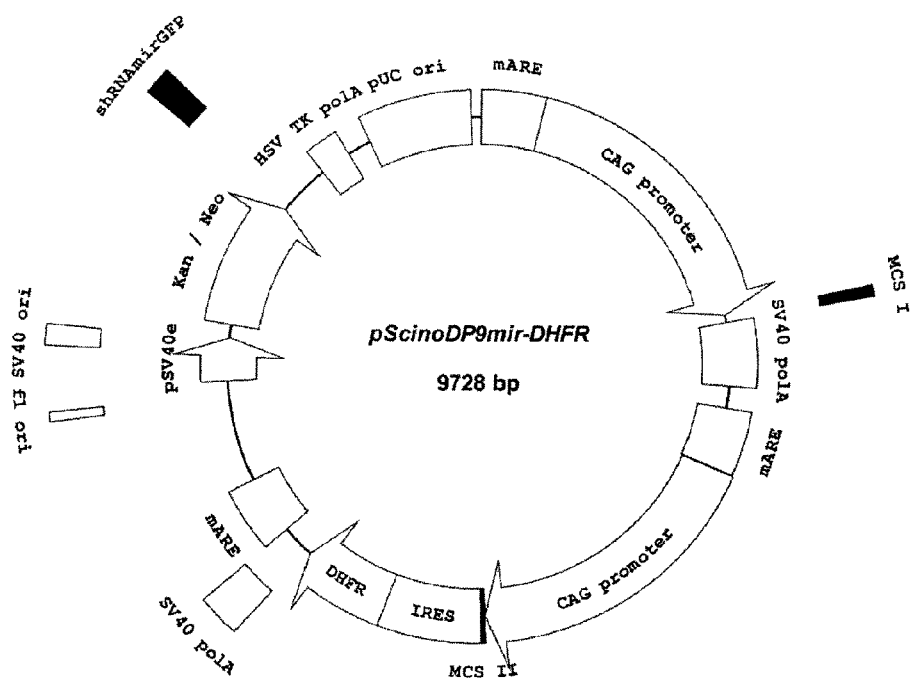
FIG. 6 is a map of expression vector pScinoDP9mir-DHFR.

The pScinoDP9mir-DHFR vector (FIG. 6) was constructed using procedures similar to those used for the construction of pScinoDP8mir-DHFR vector and substituting the two CMV enhancers in pScinoDP8mir-DHFR with CAG promoter (CMV-IE enhancer fused with chicken β-actin promoter). The complete sequence of pScinoDP9mir-DHFR is shown in SEQ ID NO:13.

pScinoDP9mir-DHFR contains the internal ribosome entry site (IRES) of the encephalomyocarditis virus (ECMV) between the MCSII and the dihydrofolate reductase (DHFR)

coding region. This permits both the gene of interest (for example: light chain cloned into the MCSII) and the DHFR gene to be translated from a single bicistronic mRNA. Sequences flanking DHFR have been converted to a Kozak consensus translation initiation site to further increase the translation efficiency in eukaryotic cells. The MCSI in pScinoDP9mir-DHFR is between the immediate early promoter of CMV (PCMV IE) and SV40 polyadenylation signals sequences. SV40 polyadenylation signals downstream of the MCSI direct proper processing of the 3' end of the first transcription. The MCSII in pScinoDP-dhfr is between the second immediate early promoter of cytomegalovirus (PCMV IE) and the IRES sequence. SV40 polyadenylation signals downstream of the DHFR gene direct proper processing of the 3' end of the bicistronic mRNA.

Because pScinoDP9mir-DHFR is derived from pEGFP-N1 vector, it contains an SV40 origin for replication in mammalian cells expressing the SV40 T antigen. A neomycin-resistance cassette (Neo$^r$), consisting of the SV40 early promoter, the neomycin/kanamycin resistance gene of Tn5, and polyadenylation signals from the Herpes simplex virus thymidine kinase (HSV TK) gene, allows stably transfected eukaryotic cells to be selected using G418. A bacterial promoter upstream of this cassette expresses kanamycin resistance in $E.\ coli$. The pScinoDP-DHFR backbone also contains a pUC origin of replication for propagation in $E.\ coli$ and an f1 origin for single-stranded DNA production.

sequence and 4-2Leader sequence were PCR amplified from oligo-synthesis skeleton fragments, while heavy chain constant region sequence of human IgG$_1$(hIgG$_1$C$_H$) and light chain constant region sequence of human IgG$_1$(hIgG$_1$C$_L$) were obtained from recombinant plasmids containing human IgG$_1$ sequence. Hybrid leader sequence and hIgG$_1$ constant region sequence vectors were obtained by sub-cloning hIgG$_1$ constant region to leader sequence containing vector by the way of orientation linkage.

Figure 7A:
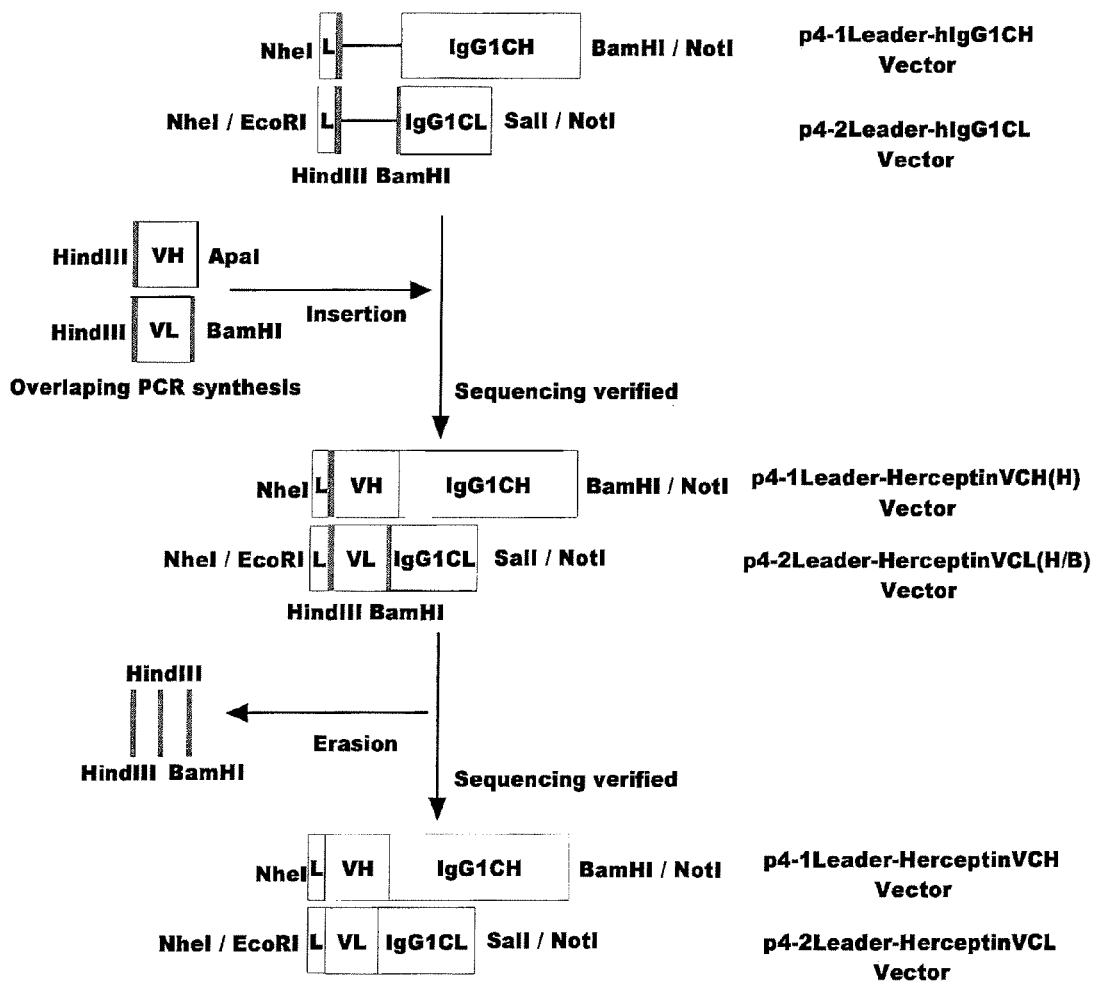
FIGS. 7A and 7B are diagrams showing the construction of expression vector pScinoDP9mir-Herceptin-DHFR.

Next, variant region of heavy chain (V$_H$) and light chain (V$_L$) were created through repeated overlapping PCR from oligo-synthesis skeleton fragments and sub-cloned into p4-1Leader-hIgG$_1$C$_H$ or p4-2Leader-hIgG$_1$C$_L$ vector. After correcting PCR errata and removing additional sequences introduced during cloning process, the correctness of the leader-peptide-HerceptinVC sequence was verified by sequencing (FIG. 7A).

Figure 7B:
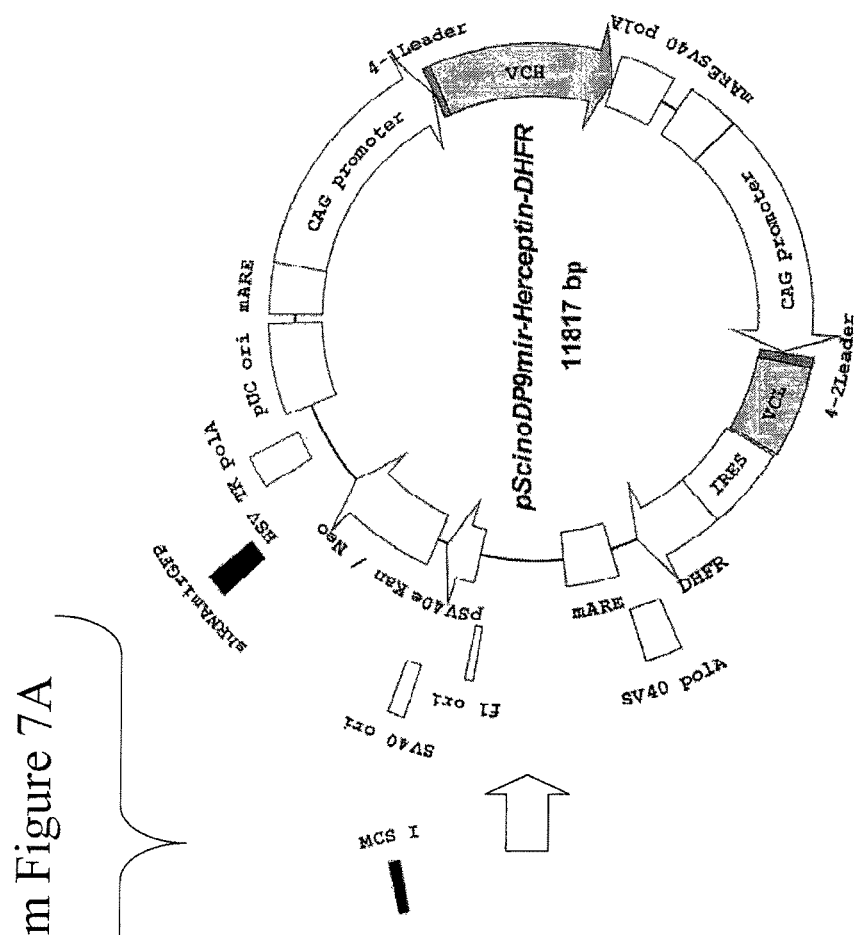
Figure 7B:
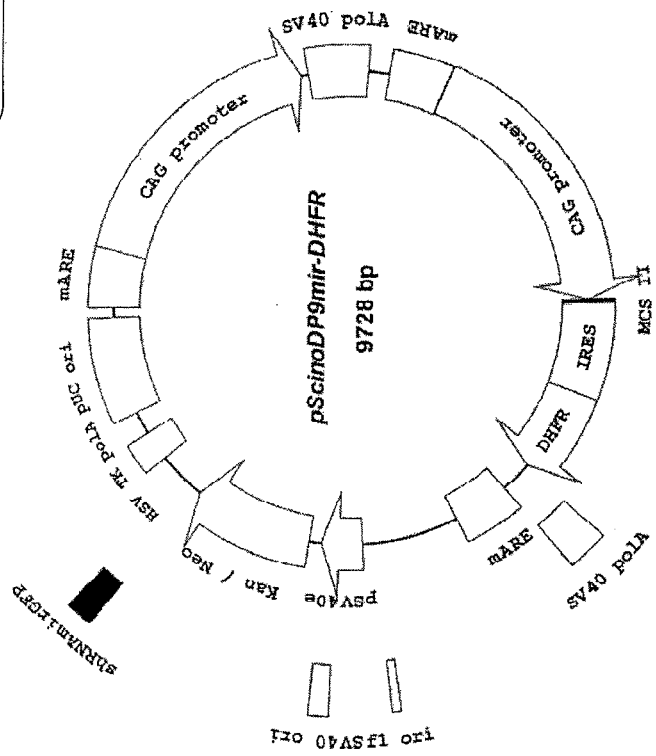

Finally, the hybrid 4-1Leader-Herceptin heavy chain (4-1-HerceptinVC$_H$), and 4-2Leader-Herceptin light chain (4-2-HerceptinVC$_L$) were individually sub-cloned into the MCSI and MCSII sites in pScinoDP9mir-DHFR vector to form the pScinoDP9mir-Herceptin-DHFR vector (FIG. 7B).

The amino acid and nucleotide sequences for the variant region of anti-HER2 heavy chain 1 are shown in SEQ ID NOS: 14 and 15, respectively. The skeleton fragments and PCR primers used for the variant region of the heavy chain (V$_H$) have the following sequences:

Skeleton Fragments:

```
HerceptinV_H-L1(+) (108 mer)
                                                    (SEQ ID NO: 16)
5'-gAggTgCAgCTCgTggAgAgTggTggCgggTTggTCCAgCCAggCgggTCTCTgCgATTgAgCTg TgCTgCCTCTggATTTAACATCAAAgACACgTACATCCATTgg-3'

HerceptinV_H-L2(-) (105 mer)
                                                    (SEQ ID NO: 17)
5'-TTTAACgCTATCAgCgTATCTggTgTAgCCgTTAgTgggATAgATTCTAgCTACCCATTC AAggCCCTTgCCgggggCCTgTCTCACCCAATggATgTACgTgTC-3'

HerceptinV_H-R1(+) (105 mer)
                                                    (SEQ ID NO: 18)
5'-TACgCTgATAgCgTTAAAggAAggTTTACTATTTCTgCCgACACCTCCAAgAATACCgC ATATCTACAgATgAACTCCCTgCgCgCTgAggACACCgCTgTgTAT-3'

HerceptinV_H-R2(-) (108 mer)
                                                    (SEQ ID NO: 19)
5'-CTTAgTAgAgCACTgCTAACTgTCACTAAggTACCCTggCCCCAgTAgTCCATTgCgTAg AATCCgTCTCCCCCCCAACgTgAgCAgTAATACACAgCggTgTCCTC-3'
```

(6) The pGFP/Puromycin Vector

IRES sequence and DHFR gene were obtained by PCR amplification used pIRES2-EGFP and pLKO-AS3w-puro plasmid as template. A hybrid IRES sequence fragment and puromycin gene fragment (IRES2-puromycin) was obtained through overlap extension by PCR(OL-PCR). The IRES2-puromycin fragment was inserted into SalI-BamHI digested pFLAG-CMV2 vector (Kodak). The resulting construct was named pIRES2-Puro. The EGFP gene was obtained from the pEGFP-N1 vector and inserted into the pIRES-Puro vector to form pGFP/Puromycin vector.

(7) The pScinoDP9mir-Herceptin-DHFR Vector

The construction of the pScinoDP9mir-Herceptin-DHFR vector is shown in FIGS. 7A and 7B. Briefly, the 4-1Leader Primers for Amplification:

```
Herceptin-V_H-5HindIII (30 mer) (sense)
                                                    (SEQ ID NO: 20)
5'-gCCAAgCTTgAggTgCAgCTCgTggAgAgT-3'

Herceptin-V_H-3ApaI (30 mer) (antisense)
                                                    (SEQ ID NO: 21)
5'-AggggGCCCTTAgTAgAggCACTgCTAACT-3'
```

The amino acid and nucleotide sequences for the variant region of anti-HER2 light chain 1 are shown in SEQ ID NOS:22 and 23, respectively. The skeleton fragments and PCR primers used for the variant region of the light chain ($V_L$) have the following sequences:

Skeleton Fragments:

HerceptinV$_L$-L1(+) (93 mer)
(SEQ ID NO: 24)
5'-gATATACAgATgACACAgTCTCCgTCAAgTCTgAgCgCAAgCgTgggCgACCggGTAACA ATTACCTgTAgAgCCAgCCAggACgTAAATACA-3'

HerceptinV$_L$-L2(-) (95 mer)
(SEQ ID NO: 25)
5'-CCgCTATAAAggAACgAggCAgAgTAgATCAgAAgCTTAggAGCTTTACCAggTTTTTgC TgATACCAggCCACggCTgTATTTACgTCCTggCT-3'

HerceptinV$_L$-R1(+) (94 mer)
(SEQ ID NO: 26)
5'-CTCgTTCCTTTATAgCggggTgCCAAgCCgCTTCTCCggATCTAggTCTggAACAgACTTT ACTCTgACCATTTCCAgTCTCCAgCCCgAAgAC-3'

HerceptinV$_L$-R2(-) (93 mer)
(SEQ ID NO: 27)
5'-CTTgATCTCgACCTTggTgCCCTgCCCAAATgTgggTggAgTCgTgTAATgTTgCTggCAAT AgTAggTAgCAAAgTCTTCgggCTggAgACT-3'

Primers for Amplification

Herceptin-V$_L$-5HindIII (30 mer) (sense)
(SEQ ID NO: 28)
5'-gCCAAgCTTgATATACAgATgACACAgTCT-3'

Herceptin-V$_L$-3BamHI (30 mer) (antisense)
(SEQ ID NO: 29)
5'-CgCggATTCCTTgATCTCgACCTTggTgCC-3'

Example 3

Establishment of Herceptin/CHO$^{+GFP/-dhfr}$ Cell Line

CHO$^{/+GFP/-dhfr}$ cells were suspended in PBS buffer. 40 μg of linearized plasmid (pScinoDP9mir-Herceptin-DHFR) DNA was added to the cells and incubated on ice for 10 min. The cells were then electroporated by two pulses at a voltage setting of 750 V and a capacitance setting at 25 μF (Gene Pulser II with capacitance extender, and pulse controller from Bio-Rad). The electroporated cells were plated in T-175 flask with 25 mL of medium (IMDM supplemented with HT, 10% FBS, 2 μM MTX and 5 μg/ml puromycin dihydrochloride) for 24 hours. The cells were then selected using 800 μg/ml of G418 sulfate (Calbiochem, Cat #345810) in Minimum Essential medium Alpha medium (Alpha-MEM, Gibco, Cat. No. 12000) supplemented with 10% D-FBS (Gibco, Cat. No. 30067-334) and 5 μg/ml of puromycin dihydrochloride. After 14 days of selection in Alpha-MEM medium supplemented with 10% D-FBS and selective antibiotics, the cells were subjected to MTX treatment at increasing concentrations for gene amplification.

The cells were FACS sorted to screen for cells with low GFP fluorescent intensity. Since the expression of the target gene and shRNA$^{GFP}$ would lead to reduced GFP production in the CHO$^{+GFP/-dhfr}$ cells, cells with least green fluorescence (GFP negative) would have the highest level of target gene expression. FACS was performed using a MoFlo™ XDP (Beckman Coulter) equipped with Summit software, an laser emitting at 488 nm and a cell deposition unit for sorting.

Low-fluorescence and high-fluorescence cell populations were sorted with the single cell deposited using FACS into 96-well cell culture plates containing 220 μl Alpha-MEM supplemented with 10% D-FBS, G418, puromycin dihydrochloride and MTX. Clones were incubated at 37° C. and 5% carbon dioxide in a humidified incubator for 12 days.

Example 4

Characterization of Herceptin/CHO$^{+GFP/-dhfr}$ Cell Line (1) Detection of Surface Antibodies by Immunostaining Trypsinized herceptin/CHO$^{+GFP/-dhfr}$ cells were centrifuged 5 min at 200 rpm. The cells were washed twice with PBS and resuspended in PBS to a final concentration of about $1 \times 10^7$ cells/ml. The cells were then incubated with phycoerythrin (PE)-conjugated mouse anti-human IgG(Fc) (Beckman Coulter, Cat. No. 736007) at dilutions according to the manufacturer's recommendations at 4° C. for 30 min in the dark, washed twice with PBS and kept on ice for FACS analysis.

(2) Detection of Secreted Antibodies by ELISA

Briefly, 96-well plates were coated with anti human IgG antibody (Sigma: I 1886) diluted in 0.05 M Carbonate-Bicarbonate buffer (pH 9.7), and incubated at 4° C. for 16 h. Plates were blocked with blocking buffer (10 mM Tris, 0.15 M NaCl, 1% skim milk, pH 8.0) at 37° C. for 30 min. Culture supernatants were loaded on the wells and incubated at 37° C. for 2 h. Horseradish peroxidase conjugated anti-human IgG-F(c) antibody (Abcam: ab7499), diluted in dilution buffer (10 mM Tris, 0.15 M NaCl, 0.05% Tween 20, pH 8.0) according to the manufacturer's recommendations and incubated at 37° C. for 1 h. The reactions were detected using the substrate (1-step™ ultra TMB-ELISA, Pierce, Cat. 34028) and plates were read on microplate reader (Bio-Rad).

(3) Results

Figure 8:
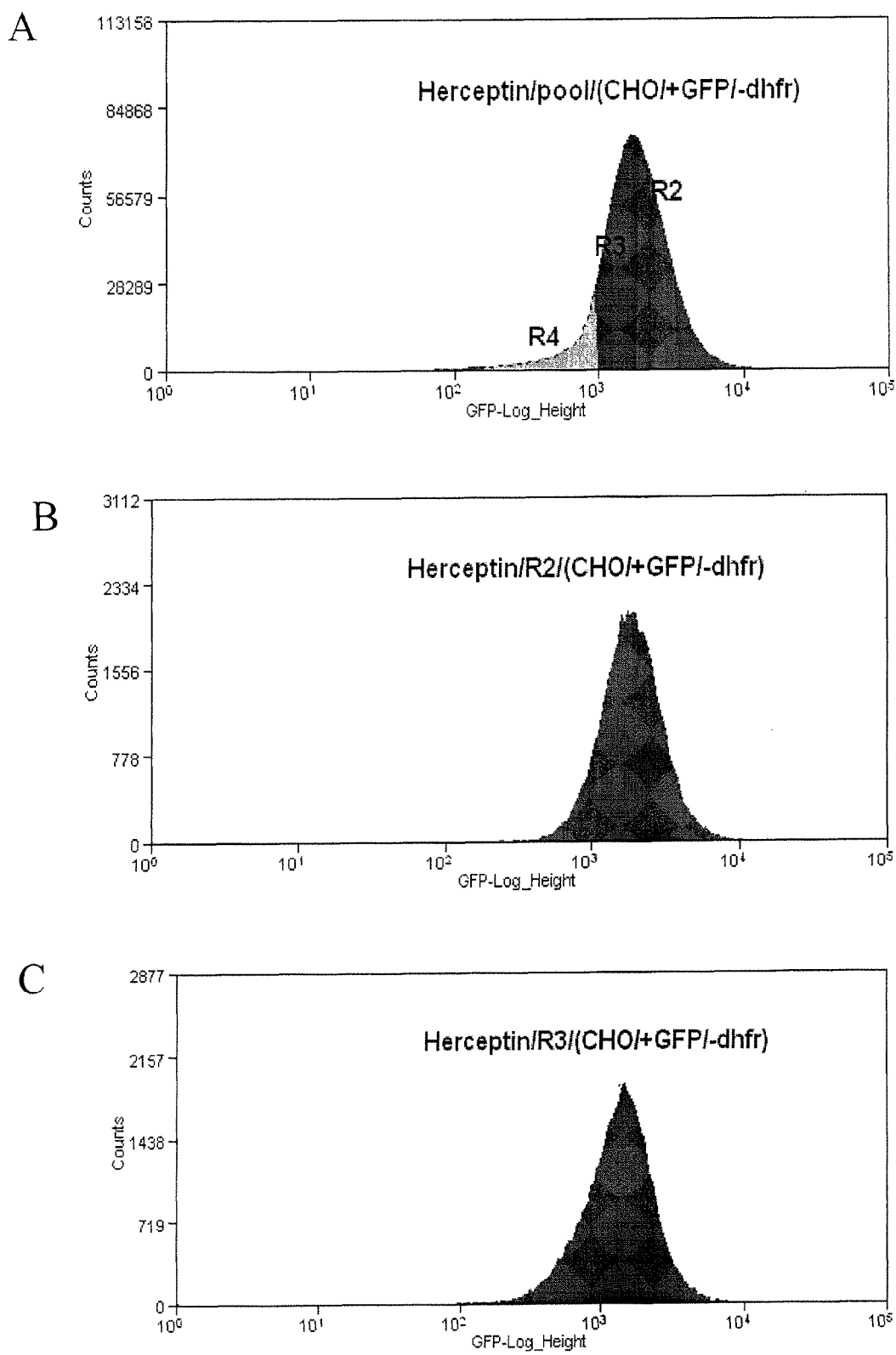
FIG. 8 is a composite of diagrams showing GFP expression and antibody expression in herceptin-CHO$^{+GFP/-dhfr}$ cells. Panel A: FACS histogram profile of herceptin-CHO$^{/+GFP/-dhfr}$ cells. Panels B-C: FACS histogram profiles of herceptin-CHO$^{/+GFP/-dhfr}$ cell sorted at different fluorescence intensity levels. Panel E: ELISA analysis of antibody production of cells sorted from different fluorescent populations.
Figure 8:
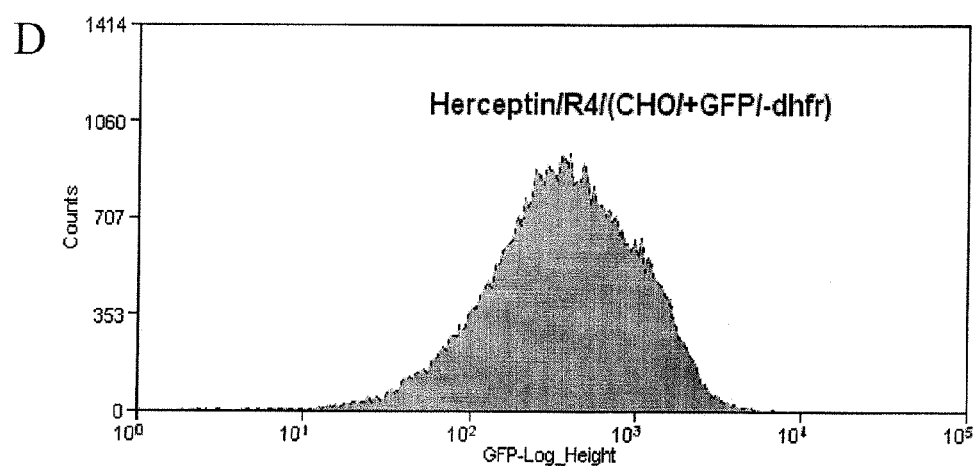
Figure 8:
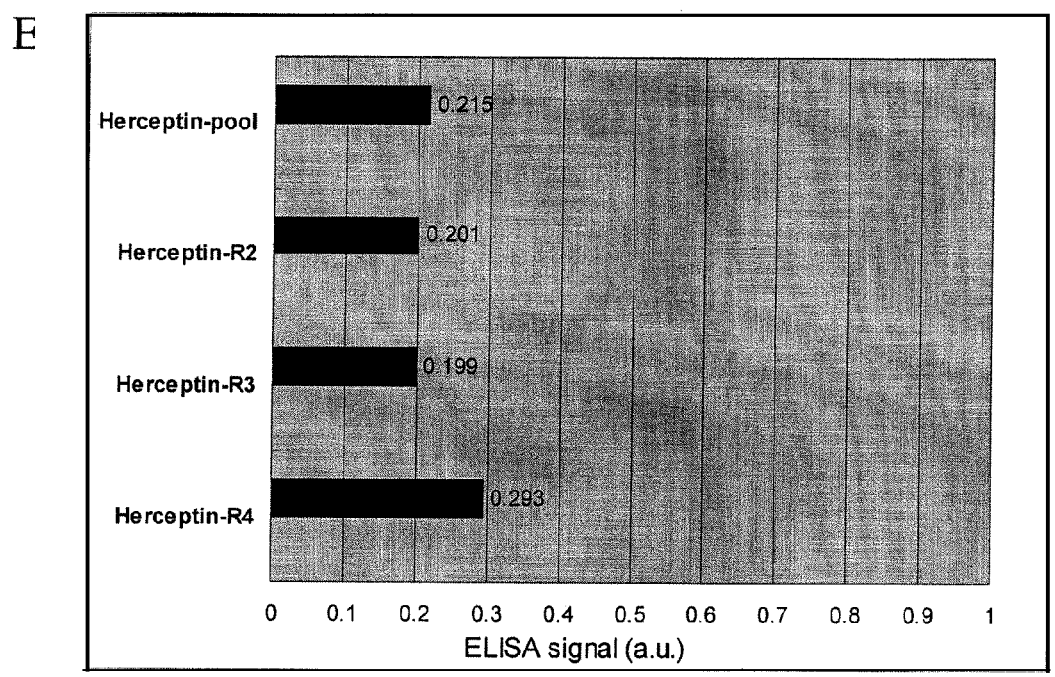

FIG. 8 presents a histogram profile of Herceptin (CHO$^{/+GFP/-dhfr}$) cells sorted at different fluorescent intensities using FACS. Panel A shows the GFP fluorescence in a pool of Herceptin CHO$^{/+GFP/-dhfr}$ cells. The cells were divided into several subpopulations (R2, R3 and R4) based on the fluorescent intensity. Panels B-D show levels of GFP expression in each sub-population. Panel E shows the anti-herceptin antibody titles in the pool and each subpopulation.

The data showed that cells with the lowest level of GFP fluorescence (Herceptin/R4/(CHO$^{/+GFP/-dhfr}$)) had the highest level of anti-herceptin titer.

Figure 9:
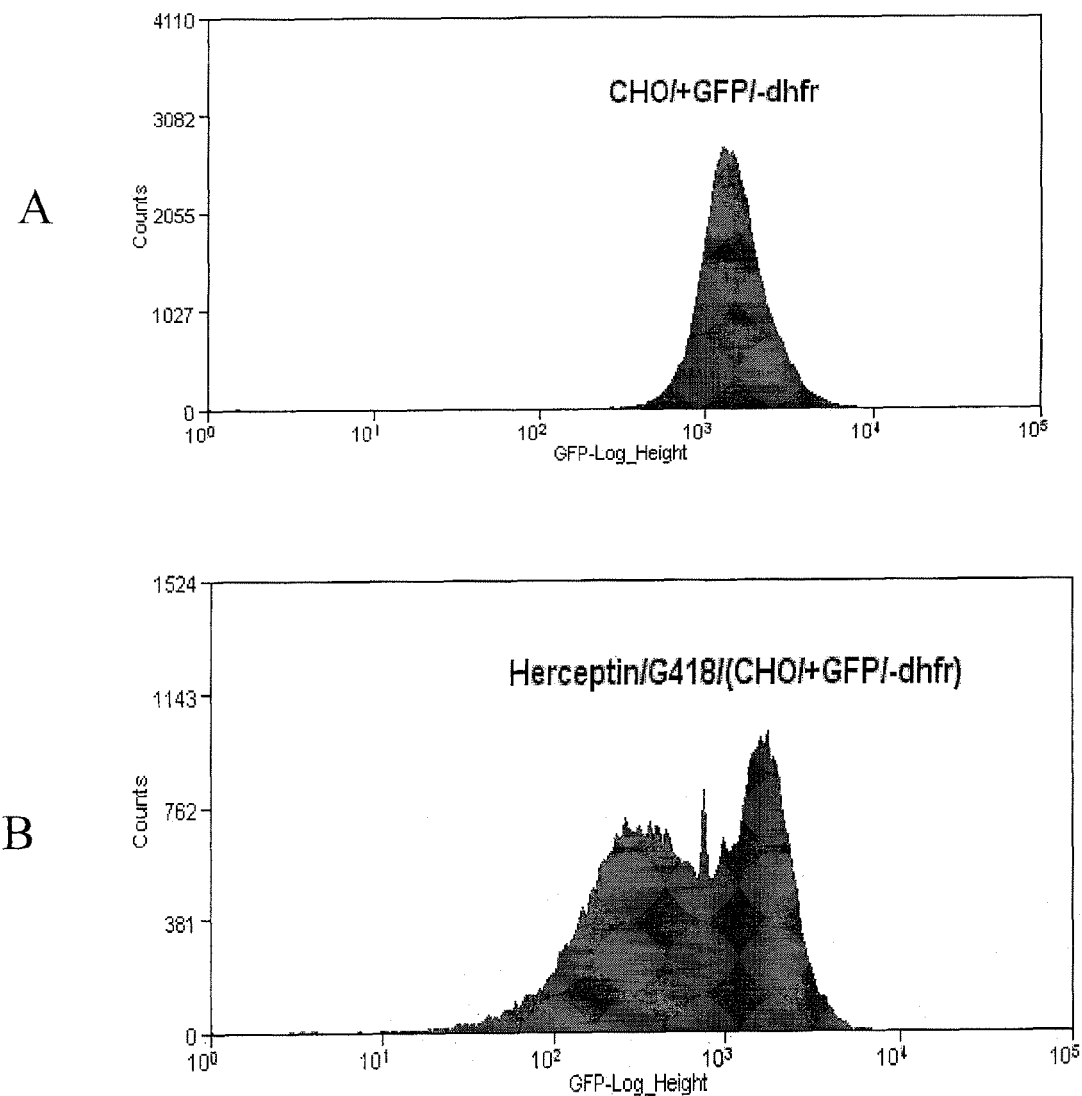
FIG. 9 is a composite of diagrams showing GFP expression in herceptin-CHO$^{+GFP/-dhfr}$ cells after multiple rounds of selection. Panel A: FACS histogram profile of CHO$^{/-dhfr}$ cells after GFP expression. Panel B: FACS histogram profile of herceptin-CHO$^{+GFP/-dhfr}$ cells after G418 selection. Panel C: FACS histogram profile of herceptin-CHO$^{/+GFP/-dhfr}$ cells after first round of MTX (100 nM) amplification. Panel D: FACS histogram profile of herceptin-CHO$^{/+GFP/-dhfr}$ cells after second round of MTX (200 nM) amplification.
Figure 9:
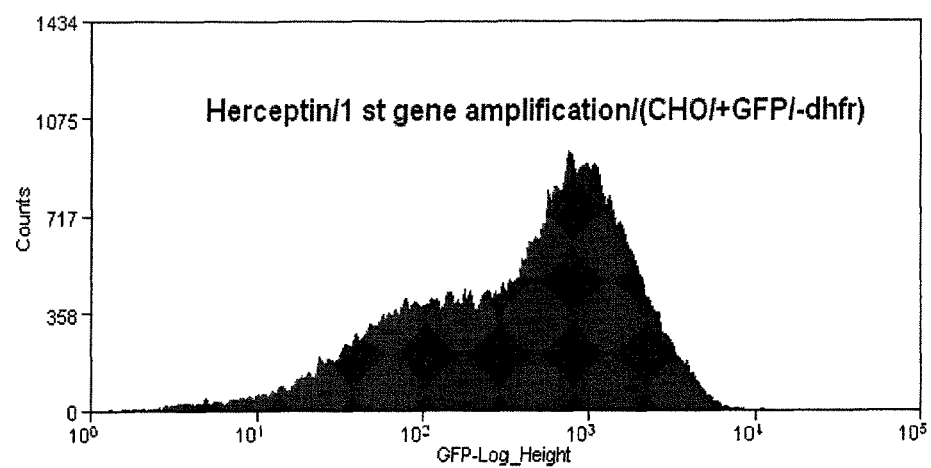
Figure 9:
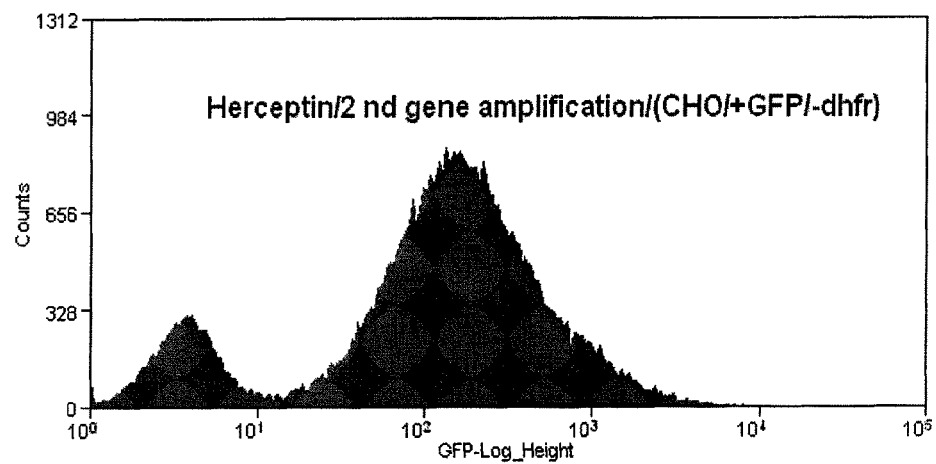

FIG. 9 shows that the GFP expression level in CHO$^{/+GFP/-dhfr}$ cells was reduced upon transfection with DNA constructs containing a target protein (Herceptin) and shRNAi$^{GFP}$. The FACS profiles indicate that the GFP expression level was further reduced after two rounds of MTX challenge (panels C and D). These results demonstrate that the level of target gene amplification correlated to GFP expression levels and the strength of gene amplification.

Figure 10:
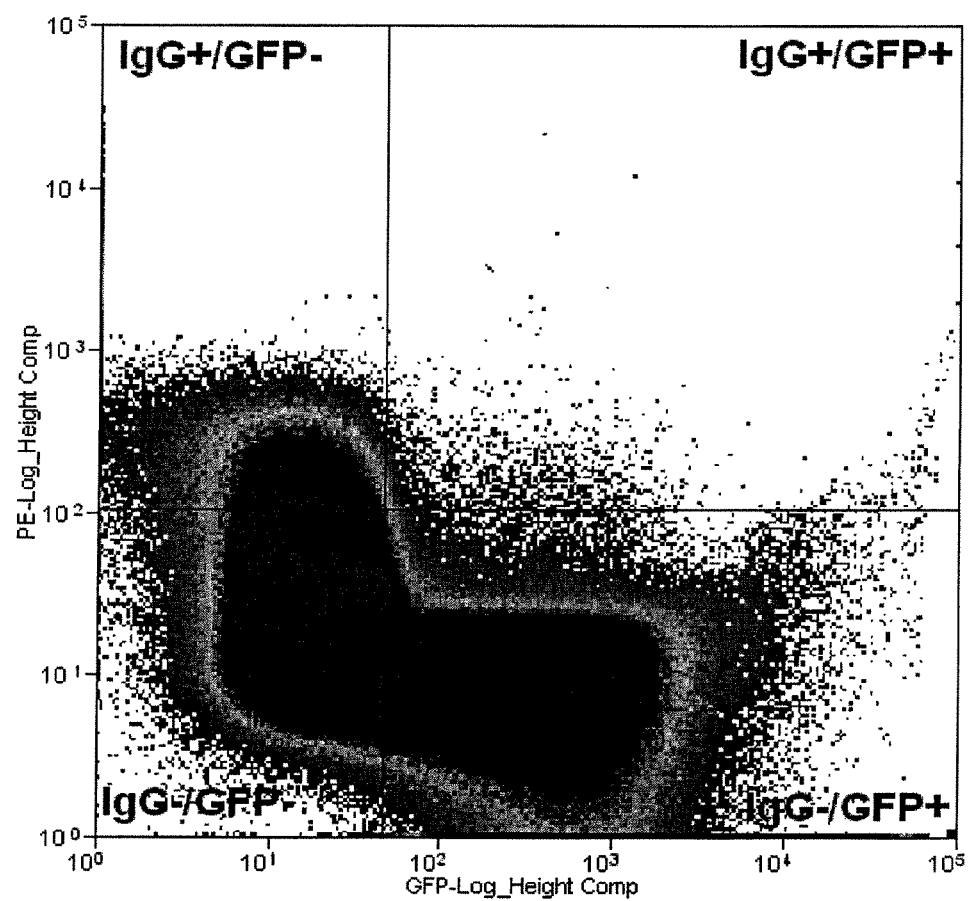
FIG. 10 is a diagram showing FACS analysis of herceptin-CHO$^{+GFP/-dhfr}$ cells stained with a PE-conjugated anti-human IgG(Fc) antibody. Cells secreting antibodies were PE positive and GFP negative according to experimental design and shown in upper-left panel. Fluorescence signal was determined by FACS and calibrated with standard compensation protocol.

FIG. 10 shows a representative FACS analysis of Herceptin/CHO$^{/+GFP/-dhfr}$ cells stained with PE-conjugated mouse anti-human IgG(Fc). The result demonstrated that the antibody-producing cells (i.e., cells with higher PE staining) exhibited low levels of GFP expression.

Figure 11:
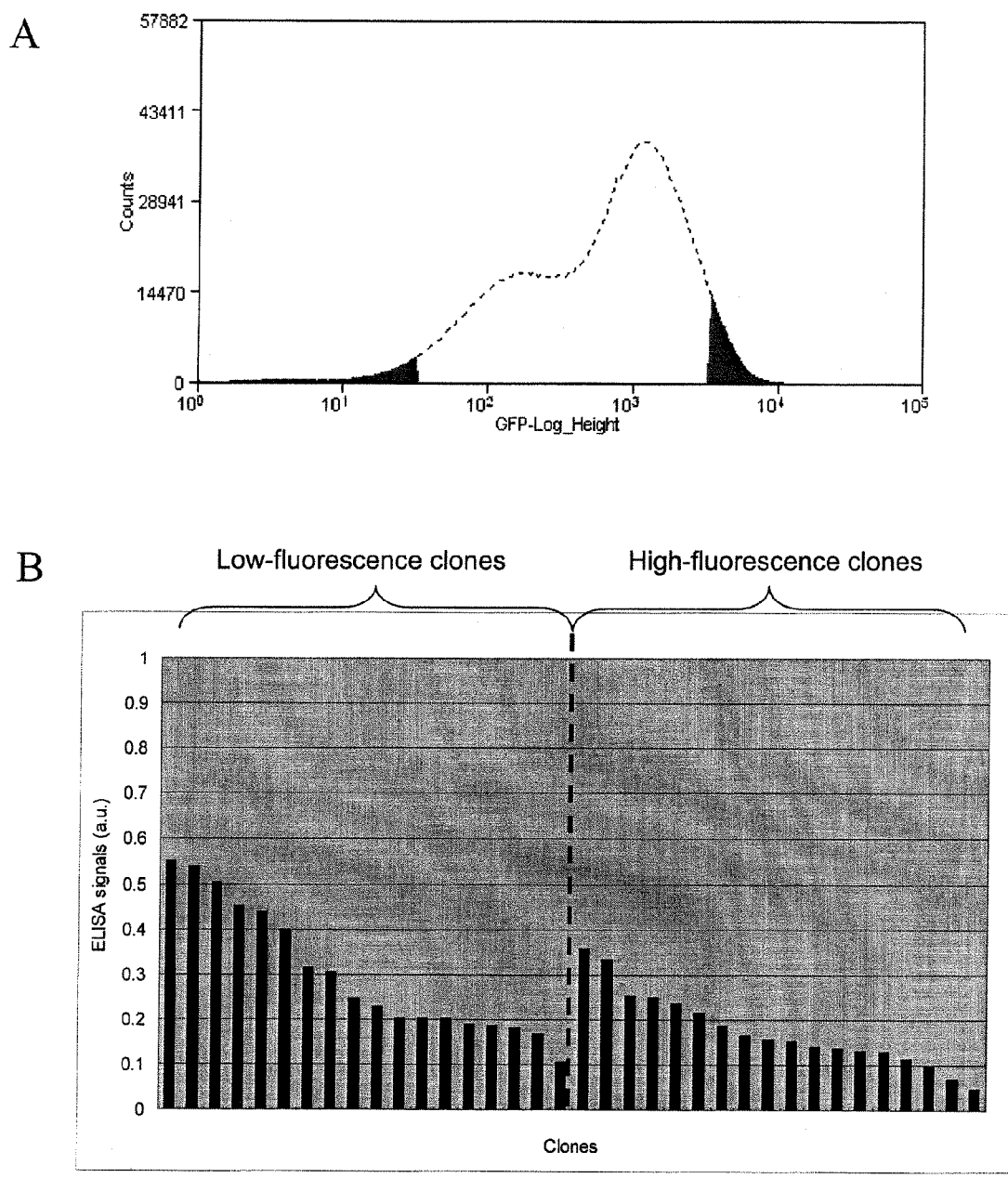
FIG. 11 shows the key features of the FACS sorting procedure for herceptin-CHO$^{+GFP/-dhfr}$ cells and ELISA results. Panel A: FACS histogram profile for Herceptin (CHO/+GFP/−dhfr) cells. Horizontal bars and gray regions indicate the low-fluorescence and high-fluorescence cell populations used for the single cell analysis. Panel B: Antibody expression levels detected by ELISA of each individual clones selected from low-fluorescence or high-fluorescence populations.

FIG. 11A shows a histogram profile for Herceptin (CHO/+GFP/-dhfr) cells. Horizontal bars and shaded regions indicate the low-fluorescence and high-fluorescence cell populations used for the single cell analysis. FIG. 11B shows that 8 out of 18 low-fluorescent cell clones yielded ELISA values greater than 0.3, while only 2 out of 18 high-fluorescent cells clones yielded ELISA values greater than 0.3. These results demonstrated that the low-fluorescent cell population contains a higher frequency of high-yield antibody producing cells and confirmed the reversal GFP-based screen strategy.

Figure 12:
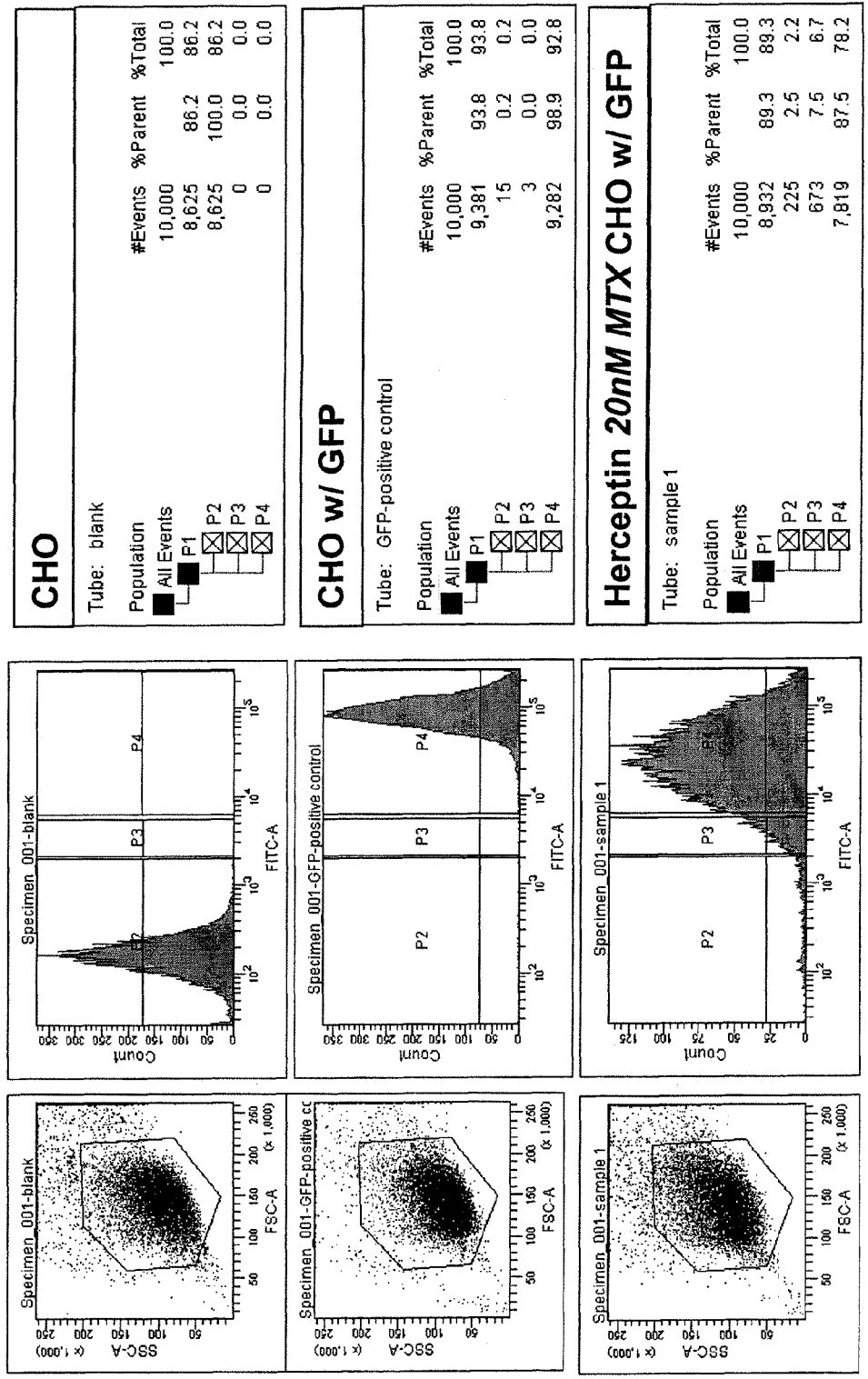
FIG. 12 is a composite of diagrams showing FACS analysis of GFP expression in cells transfected with DNA constructs encoding shRNA$^{GFP}$ and Herceptin.

FIG. 12 shows that GFP expression in CHO$^{+GFP/-dhfr}$ cells is reduced by the transfection of the DNA construct encoding Herceptin and shRNA$^{GFP}$.

(4) Conclusion

The use of the shRNAmir$^{eGFP}$ coupled with flow cytometry substantially improves the accuracy and efficiency of cell line development at two crucial points. First, for early stage clone screening, the FACS method is a better predictor of clone productivity than the analysis of conditioned media for therapeutic protein titer. Second, clones with unstable transgene expression are easily identified by an observed increase in fluorescence during amplification stage. Thus, the present method provides the novel benefits of accurate 96-well clone screening to identify good candidates for further development and elimination of unstable clones at an earlier stage in the development process than traditional methods.

These results demonstrate that the DNA constructs and screening methods of the present invention reliably yield high-expression clones homogenous protein preparations. Since the isolation of mammalian cell lines capable of high-yield expression of recombinant antibodies is not performed by screening multiple individual clones with limiting dilution techniques, the procedure is less labor-intensive and may significantly reduce the time required to generate clones for bioproduction. The procedure requires no additional reagent for clone selection and offers additional benefits to monitor genome stability. The expression level of the target gene is also more correlative to the strength of amplification gene. The bicistronic design allows synchronously expressions of two foreign genes in the same chromosome. The inhibitive approach enhance the intensity of the target gene amplification by reducing the intensity of the reporter gene amplification. The use of ARE increases the expression of the foreign recombinant protein by eliminating the difference caused by the inhibition of inserting the foreign gene into the different chromosome areas.

What is claimed is:

1. An expression vector for high-throughput screening of cells harboring the expression vector, comprising:
 a first nucleotide sequence, wherein the first nucleotide sequence is a transgene encoding a therapeutic molecule;
 a second nucleotide sequence encoding an exogenous selection marker for a host cell;
 a third nucleotide sequence encoding an inhibitor to an endogenous selection marker in the host cell; and
 one or more regulatory elements that control the expression of the first, second and third nucleotide sequences in the host cell,
 wherein the first nucleotide sequence is linked to the second nucleotide sequence by an internal ribosome entry site (IRES).

2. The expression vector of claim 1, further comprising one or more anti-repressor elements.

3. The expression vector of claim 2, wherein the one or more anti-repressor elements includes a partial mouse anti-repressor element 40.

4. The expression vector of claim 1, wherein the inhibitor is an interfering RNA.

5. The expression vector of claim 4, wherein the interfering RNA is a miR-30-based shRNA.

6. The expression vector of claim 1, wherein the endogenous selection marker is a fluorescent protein.

7. The expression vector of claim 6, wherein the fluorescent protein is green fluorescent protein.

8. The expression vector of claim 1, wherein the exogenous selectable marker is dihydrofolate reductase.

9. The expression vector of claim 1, wherein the one or more regulatory elements include a CMV IE enhancer.

10. The expression vector of claim 1, wherein the therapeutic molecule is Herceptin.

* * * * *

SEQUENCE LISTING

```
<160> NUMBER OF SEQ ID NOS: 29

<210> SEQ ID NO 1
<211> LENGTH: 97
<212> TYPE: DNA
<213> ORGANISM: artificial
<220> FEATURE:
<223> OTHER INFORMATION: synthetic oligo

<400> SEQUENCE: 1
tgctgttgac agtgagcgag cacaagctgg agtacaacta tagtgaagcc acagatgtat      60
agttgtactc cagcttgtgc ctgcctactg cctcgga                              97

<210> SEQ ID NO 2
<211> LENGTH: 40
<212> TYPE: DNA
<213> ORGANISM: artificial
<220> FEATURE:
<223> OTHER INFORMATION: synthetic oligo

<400> SEQUENCE: 2
cagaaggacc ggtaaggtat attgctgttg acagtgagcg                           40

<210> SEQ ID NO 3
<211> LENGTH: 37
<212> TYPE: DNA
<213> ORGANISM: artificial
<220> FEATURE:
<223> OTHER INFORMATION: synthetic oligo

<400> SEQUENCE: 3
```
ctaaagtagc cccttaagct ttccgaggca gtaggca    37

<210> SEQ ID NO 4
<211> LENGTH: 106
<212> TYPE: DNA
<213> ORGANISM: artificial
<220> FEATURE:
<223> OTHER INFORMATION: synthetic oligo

<400> SEQUENCE: 4
ttgctctgag ccagcccacc agtttggaat gactcctttt tatgacttga attttcaagt    60
ataaagtcta gtgctaaatt taatttgaac aactgtatag tttttg    106

<210> SEQ ID NO 5
<211> LENGTH: 106
<212> TYPE: DNA
<213> ORGANISM: artificial
<220> FEATURE:
<223> OTHER INFORMATION: synthetic oligo

<400> SEQUENCE: 5
ttagaaatcc tcacacacaa caagttttca tttcacttct aattctgaaa aaaacactgc    60
caccattttt tttccttccc ccaaccagca aaaactatac agttgt    106

<210> SEQ ID NO 6
<211> LENGTH: 106
<212> TYPE: DNA
<213> ORGANISM: artificial
<220> FEATURE:
<223> OTHER INFORMATION: synthetic oligo

<400> SEQUENCE: 6
gtgtgtgagg atttctaatg acatgtggtg gttgcatact gagtgaagcc ggtgagcatt    60
ctgccatgtc accccctcgt gctcagtaat gtactttaca gaaatc    106

<210> SEQ ID NO 7
<211> LENGTH: 106
<212> TYPE: DNA
<213> ORGANISM: artificial
<220> FEATURE:
<223> OTHER INFORMATION: synthetic oligo

<400> SEQUENCE: 7
tggcagaaat gcaggctgag tgagactacc cagagaagag accggatata cacaagaagc    60
atggtttata tcaatctttt gagtttagga tttctgtaaa gtacat    106

<210> SEQ ID NO 8
<211> LENGTH: 25
<212> TYPE: DNA
<213> ORGANISM: artificial
<220> FEATURE:
<223> OTHER INFORMATION: synthetic oligo

<400> SEQUENCE: 8
ttgctctgag ccagcccacc agttt    25

<210> SEQ ID NO 9
<211> LENGTH: 30
<212> TYPE: DNA
<213> ORGANISM: artificial
<220> FEATURE:
<223> OTHER INFORMATION: synthetic oligo

<400> SEQUENCE: 9

```
gttattaatt ggcagaaatg caggctgagt                                      30
```

<210> SEQ ID NO 10
<211> LENGTH: 30
<212> TYPE: DNA
<213> ORGANISM: artificial
<220> FEATURE:
<223> OTHER INFORMATION: synthetic oligo

<400> SEQUENCE: 10

```
cccacatgtt ggcagaaatg caggctgagt                                      30
```

<210> SEQ ID NO 11
<211> LENGTH: 30
<212> TYPE: DNA
<213> ORGANISM: artificial
<220> FEATURE:
<223> OTHER INFORMATION: synthetic oligo

<400> SEQUENCE: 11

```
ggactagttg gcagaaatgc aggctgagtg                                      30
```

<210> SEQ ID NO 12
<211> LENGTH: 370
<212> TYPE: DNA
<213> ORGANISM: Mus musculus

<400> SEQUENCE: 12

```
ttgctctgag ccagcccacc agtttggaat gactcctttt tatgacttga attttcaagt     60
ataaagtcta gtgctaaatt taatttgaac aactgtatag ttttttgctgg ttgggggaag   120
gaaaaaaat ggtggcagtg ttttttttcag aattagaagt gaaatgaaaa cttgttgtgt    180
gtgaggattt ctaatgacat gtggtggttg catactgagt gaagccggtg agcattctgc   240
catgtcaccc cctcgtgctc agtaatgtac tttacagaaa tcctaaactc aaaagattga   300
tataaaccat gcttcttgtg tatatccggt ctcttctctg ggtagtctca ctcagcctgc   360
atttctgcca                                                          370
```

<210> SEQ ID NO 13
<211> LENGTH: 9729
<212> TYPE: DNA
<213> ORGANISM: artificial
<220> FEATURE:
<223> OTHER INFORMATION: plasmid

<400> SEQUENCE: 13

```
ttgctctgag ccagcccacc agtttggaat gactcctttt tatgacttga attttcaagt     60
ataaagtcta gtgctaaatt taatttgaac aactgtatag ttttttgctgg ttgggggaag   120
gaaaaaaat ggtggcagtg ttttttttcag aattagaagt gaaatgaaaa cttgttgtgt    180
gtgaggattt ctaatgacat gtggtggttg catactgagt gaagccggtg agcattctgc   240
catgtcaccc cctcgtgctc agtaatgtac tttacagaaa tcctaaactc aaaagattga   300
tataaaccat gcttcttgtg tatatccggt ctcttctctg ggtagtctca ctcagcctgc   360
atttctgcca attaatagta atcaattacg gggtcattag ttcatagccc atatatggag   420
ttccgcgtta cataacttac ggtaaatggc ccgcctggct gaccgcccaa cgacccccgc   480
ccattgacgt caataatgac gtatgttccc atagtaacgc caatagggac tttccattga   540
cgtcaatggg tggagtattt acggtaaact gcccacttgg cagtacatca agtgtatcat   600
atgccaagta cgcccctat tgacgtcaat gacggtaaat ggcccgcctg gcattatgcc   660
```

```
cagtacatga ccttatggga cttccctact tggcagtaca tctacgtatt agtcatcgct    720
attaccatgg tcgaggtgag ccccacgttc tgcttcactc tccccatctc ccccccctcc    780 ccaccccaa ttttgtattt atttattttt taattatttt gtgcagcgat ggggggcgggg   840 gggggggggg cgcgcgccag gcggggcggg gcggggcgag gggcggggcg gggcgaggcg    900
gagaggtgcg gcggcagcca atcagagcgg cgcgctccga aagtttcctt ttatggcgag    960 gcggcggcg cggcggccct ataaaaagcg aagcgcgcgg cgggcgggag tcgctgcgtt    1020
gccttcgccc cgtgcccgc tccgcgccgc ctcgcgccgc ccgccccggc tctgactgac    1080
cgcgttactc ccacaggtga gcgggcggga cggcccttct cctccgggct gtaattagcg    1140
cttggtttaa tgacggctcg tttcttttct gtggctgcgt gaaagcctta aagggctccg    1200
ggagggccct ttgtgcgggg gggagcggct cggggggtgc gtgcgtgtgt gtgtgcgtgg    1260
ggagcgccgc gtgcggcccg cgctgcccgg cggctgtgag cgctgcgggc gcggcgcggg    1320
gctttgtgcg ctccgcgtgt gcgcgagggg agcgcggccg ggggcggtgc cccgcggtgc    1380 ggggggggctg cgagggaac aaaggctgcg tgcggggtgt gtgcgtgggg gggtgagcag    1440
ggggtgtggg cgcggcggtc gggctgtaac ccccccctgc aacccctcc ccgagttgct    1500 gagcacggcc cggcttcggg tgcggggctc cgtacggggc gtggcgcggg gctcgccgtg    1560
ccggggcggg ggtggcggca ggtgggggtg ccggccgggg cggggccgcc tcgggccggg    1620
gagggctcgg gggaggggcg cggcggcccc cggagcgccg gcggctgtcg aggcgcggcg    1680
agccgcagcc attgccttt atggtaatcg tgcgagaggg cgcagggact tcctttgtcc    1740
caaatctgtg cggagccgaa atctggagg cgccgccgca cccccctctag cgggcgcggg    1800 gcgaagcggt gcggcgccgg caggaaggaa atgggcgggg agggccttcg tgcgtcgccg    1860
cgccgccgtc cccttctccc tctccagcct cggggctgtc cgcgggggga cggctgcctt    1920 cggggggac ggggcagggc ggggttcggc ttctggcgtg tgaccggcgg ctctagagcc    1980
tctgctaacc atgttcatgc cttcttcttt ttcctacagc tcctgggcaa cgtgctggtt    2040
attgtgctgt ctcatcattt tggcaaagaa tttaatacga ctcactatag ggagacccaa    2100
gctggctagc gctaccggac tcagatctcg aggccggcaa ggccggatcc agacatgata    2160
agatacattg atgagtttgg acaaaccaca actagaatgc agtgaaaaaa atgctttatt    2220
tgtgaaattt gtgatgctat tgctttattt gtaaccatta aagctgcaa taaacaagtt    2280 aacaacaaca attgcattca ttttatgttt caggttcagg gggaggtggg gaggttttt    2340 aaagcaagta aaacctctac aaatgtggta tggctgatta tgatccggct gcctcgcgcg    2400
tttcggtgat gacggtgaaa acctctgaca catgcagctc ccggagacgg tcacagcttg    2460
tctgtaagcg gatgccggga gcagacaagc ccgtcagggc gcgtcagcgg gtgttggcgg    2520
gtgtcggggc gcagccatga ggggtaccat acattgaatc aatattggca attagccata    2580
ttagtcattg gttatatagc ataaatcaat attggctatt ggccattgca tacgttgtat    2640
ctatatcata atatgtacat ttatattggc tcatgtccaa tatgattgc tctgagccag    2700 cccaccagtt tggaatgact cctttttatg acttgaattt tcaagtataa agtctagtgc    2760
taaatttaat ttgaacaact gtatagtttt tgctggttgg gggaaggaaa aaaaatggtg    2820
gcagtgtttt tttcagaatt agaagtgaaa tgaaaacttg ttgtgtgtga ggatttctaa    2880
tgacatgtgg tggttgcata ctgagtgaag ccggtgagca ttctgccatg tcaccccctc    2940
gtgctcagta atgtactta cagaaatcct aaactcaaaa gattgatata aaccatgctt    3000
cttgtgtata tccggtctct tctctgggta gtctcactca gcctgcattt ctgccaacta    3060
```

```
gtaatagtaa tcaattacgg ggtcattagt tcatagccca tatatggagt tccgcgttac    3120
ataacttacg gtaaatggcc cgcctggctg accgcccaac gacccccgcc cattgacgtc    3180
aataatgacg tatgttccca tagtaacgcc aatagggact ttccattgac gtcaatgggt    3240
ggagtattta cggtaaactg cccacttggc agtacatcaa gtgtatcata tgccaagtac    3300
gccccctatt gacgtcaatg acggtaaatg gcccgcctgg cattatgccc agtacatgac    3360
cttatgggac tttcctactt ggcagtacat ctacgtatta gtcatcgcta ttaccatggt    3420
cgaggtgagc cccacgttct gcttcactct ccccatctcc cccccctccc cacccccaat    3480
tttgtattta tttatttttt aattattttg tgcagcgatg ggggcggggg ggggggggcg    3540
gcgcgccagg cggggcgggg cggggcgagg ggcggggcgg ggcgaggcgg agaggtgcgg    3600
cggcagccaa tcagagcggc gcgctccgaa agtttccttt tatggcgagg cggcggcggc    3660
ggcggcccta taaaaagcga agcgcgcggc gggcgggagt cgctgcgttg ccttcgcccc    3720
gtgccccgct ccgcgccgcc tcgcgccgcc cgccccggct ctgactgacc gcgttactcc    3780
cacaggtgag cgggcgggac ggcccttctc ctccgggctg taattagcgc ttggtttaat    3840
gacggctcgt ttcttttctg tggctgcgtg aaagccttaa agggctccgg gagggccctt    3900
tgtgcggggg ggagcggctc gggggggtgcg tgcgtgtgtg tgtgcgtggg gagcgccgcg    3960
tgcggcccgc gctgcccggc ggctgtgagc gctgcgggcg cggcgcgggg ctttgtgcgc    4020
tccgcgtgtg cgcgagggga gcggccggg gggcggtgcc ccgcggtgcg ggggggctgc    4080
gaggggaaca aaggctgcgt gcgggtgtg tgcgtggggg ggtgagcagg gggtgtgggc    4140
gcggcggtcg ggctgtaacc cccccctgca acccctccc cgagttgctg agcacggccc    4200
ggcttcgggt gcggggctcc gtacggggcg tggcgcgggg ctcgccgtgc cgggcggggg    4260
gtggcggcag gtggggtgc cggcggggc ggggccgcct cgggccgggg agggctcggg    4320
ggaggggcgc ggcggccccc ggagcgccgg cggctgtcga ggcgcggcga gccgcagcca    4380 ttgccttta tggtaatcgt gcgagagggc gcagggactt cctttgtccc aaatctgtgc    4440
ggagccgaaa tctgggaggc gccgccgcac ccctctagc gggcgcgggg cgaagcggtg    4500
cggcgccggc aggaaggaaa tgggcgggga gggccttcgt gcgtcgccgc gccgccgtcc    4560
ccttctccct ctccagcctc ggggctgtcc gcggggggac ggctgccttc gggggggacg    4620
gggcagggcg gggttcggct tctggcgtgt gaccggcggc tctagagcct ctgctaacca    4680
tgttcatgcc ttcttctttt tcctacagct cctgggcaac gtgctggtta ttgtgctgtc    4740
tcatcatttt ggcaaagaat ttaatacgac tcactatagg gagacccaag ctggctagag    4800
cttcgaattc tgcagtcgac agatccaccg gtgcccctct ccctcccccc ccctaacgt    4860 tactggccga agccgcttgg aataaggccg gtgtgcgttt gtctatatgt tattttccac    4920
catattgccg tcttttggca atgtgagggc ccggaaacct ggccctgtct tcttgacgag    4980
cattcctagg ggtctttccc ctctcgccaa aggaatgcaa ggtctgttga atgtcgtgaa    5040
ggaagcagtt cctctggaag cttcttgaag acaaacaacg tctgtagcga ccctttgcag    5100
gcagcggaac cccccacctg cgacaggtg cctctgcggc caaaagccac gtgtataaga    5160
tacacctgca aaggcggcac aaccccagtg ccacgttgtg agttggatag ttgtggaaag    5220
agtcaaatgg ctctcctcaa gcgtattcaa caaggggctg aaggatgccc agaaggtacc    5280
ccattgtatg ggatctgatc tggggcctcg gtaacatgct ttacatgtgt ttagtcgagg    5340
ttaaaaaaac gtctaggccc cccgaaccac ggggacgtgg ttttcctttg aaaaacacga    5400
tgataatatg gccacaacca tggttcgacc attgaactgc atcgtcgccg tgtcccaaaa    5460
```

```
tatgggatt ggcaagaacg gagacctacc ctggcctccg ctcaggaacg agttcaagta   5520
cttccaaaga atgaccacaa cctcttcagt ggaaggtaaa cagaatctgg tgattatggg   5580
taggaaaacc tggttctcca ttcctgagaa gaatcgacct ttaaaggaca gaattaatat   5640
agttctcagt agagaactca aagaaccacc acgaggagct cattttcttg ccaaaagttt   5700
ggatgatgcc ttaagactta ttgaacaacc ggaattggca agtaaagtag acatggtttg   5760
gatagtcgga ggcagttctg tttaccagga agccatgaat caaccaggcc acctcagact   5820
ctttgtgaca aggatcatgc aggaatttga aagtgacacg ttttcccag aaattgattt    5880 ggggaaatat aaacttctcc cagaataccc aggcgtcctc tctgaggtcc aggaggaaaa   5940
aggcatcaag tataagtttg aagtctacga gaagaaagac taagcggccg cgactctaga   6000
tcataatcag ccataccaca tttgtagagg ttttacttgc tttaaaaaac ctcccacacc   6060
tccccctgaa cctgaaacat aaaatgaatg caattgttgt tgttaacttg tttattgcag   6120
cttataatgg ttacaaataa agcaatagca tcacaaattt cacaaataaa gcattttttt   6180
cactgcattc tagtttgctc tgagccagcc caccagtttg gaatgactcc tttttatgac   6240
ttgaattttc aagtataaag tctagtgcta aatttaattt gaacaactgt atagttttg    6300 ctggttgggg gaaggaaaaa aaatggtggc agtgtttttt tcagaattag aagtgaaatg   6360
aaaacttgtt gtgtgtgagg atttctaatg acatgtggtg gttgcatact gagtgaagcc   6420
ggtgagcatt ctgccatgtc accccctcgt gctcagtaat gtactttaca gaaatcctaa   6480
actcaaaaga ttgatataaa ccatgcttct tgtgtatatc cggtctcttc tctgggtagt   6540
ctcactcagc ctgcatttct gccacttaag gcgtaaattg taagcgttaa tattttgtta   6600
aaattcgcgt taaattttg ttaaatcagc tcatttttta accataggc cgaaatcggc     6660 aaaatccctt ataaatcaaa agaatagacc gagatagggt tgagtgttgt tccagtttgg   6720
aacaagagtc cactattaaa gaacgtggac tccaacgtca aagggcgaaa accgtctat    6780 cagggcgatg gcccactacg tgaaccatca ccctaatcaa gttttttggg gtcgaggtgc   6840
cgtaaagcac taaatcggaa ccctaaaggg agccccgat ttagagcttg acggggaaag    6900
ccggcgaacg tggcgagaaa ggaagggaag aaagcgaaag gagcgggcgc tagggcgctg   6960
gcaagtgtag cggtcacgct gcgcgtaacc accacccg ccgcgcttaa tgcgccgcta     7020
cagggcgcgt caggtggcac ttttcgggga aatgtgcgcg gaacccctat tgtttattt    7080 ttctaaatac attcaaatat gtatccgctc atgagacaat aaccctgata atgcttcaa    7140 taatattgaa aaaggaagag tcctgagcg gaaagaacca gctgtggaat gtgtgtcagt    7200
tagggtgtgg aaagtcccca ggctccccag caggcagaag tatgcaaagc atgcatctca   7260
attagtcagc aaccaggtgt ggaaagtccc caggctcccc agcaggcaga agtatgcaaa   7320
gcatgcatct caattagtca gcaaccatag tcccgcccct aactccgccc atcccgcccc   7380
taactccgcc cagttccgcc cattctccgc cccatggctg actaattttt tttatttatg   7440
cagaggccga ggccgcctcg gcctctgagc tattccagaa gtagtgagga ggcttttttg   7500
gaggcctagg cttttgcaaa gatcgatcaa gagacaggat gaggatcgtt tcgcatgatt   7560
gaacaagatg gattgcacgc aggttctccg gccgcttggg tggagaggct attcggctat   7620
gactgggcac aacagacaat cggctgctct gatgccgccg tgttccggct gtcagcgcag   7680
gggcgcccgg ttcttttgt caagaccgac ctgtccggtg ccctgaatga actgcaagac    7740
gaggcagcgc ggctatcgtg gctggccacg acgggcgttc cttgcgcagc tgtgctcgac   7800
gttgtcactg aagcgggaag ggactggctg ctattgggcg aagtgccggg gcaggatctc   7860
```

```
ctgtcatctc accttgctcc tgccgagaaa gtatccatca tggctgatgc aatgcggcgg      7920
ctgcatacgc ttgatccggc tacctgccca ttcgaccacc aagcgaaaca tcgcatcgag      7980
cgagcacgta ctcggatgga agccggtctt gtcgatcagg atgatctgga cgaagagcat      8040
caggggctcg cgccagccga actgttcgcc aggctcaagg cgagcatgcc cgacggcgag      8100
gatctcgtcg tgacccatgg cgatgcctgc ttgccgaata tcatggtgga aaatggccgc      8160 tttttctggat tcatcgactg tggccggctg ggtgtggcgg accgctatca ggacatagcg      8220
ttggctaccc gtgatattgc tgaagagctt ggcggcgaat gggctgaccg cttcctcgtg      8280
ctttacggta tcgccgctcc cgattcgcag cgcatcgcct tctatcgcct tcttgacgag      8340
ttcttctgag cgggacaccg gtaaggtata ttgctgttga cagtgagcga gcacaagctg      8400
gagtacaact atagtgaagc cacagatgta tagttgtact ccagcttgtg cctgcctact      8460
gcctcggaaa gcttaagggg ctactttaga tcacgagatt tcgattccac cgccgccttc      8520
tatgaaaggt tgggcttcgg aatcgttttc cgggacgccg gctggatgat cctccagcgc      8580
ggggatctca tgctggagtt cttcgcccac cctaggggga ggctaactga acacggaag      8640 gagacaatac cggaaggaac ccgcgctatg acggcaataa aaagacagaa taaaacgcac      8700
ggtgttgggt cgtttgttca taaacgcggg gttcggtccc agggctggca ctctgtcgat      8760
accccaccga gaccccattg gggccaatac gcccgcgttt cttccttttc cccaccccac      8820
cccccaagtt cgggtgaagg cccagggctc gcagccaacg tcgggcggc aggccctgcc      8880 atagcctcag gttactcata tatactttag attgatttaa aacttcattt ttaatttaaa      8940
aggatctagg tgaagatcct ttttgataat ctcatgacca aaatccctta acgtgagttt      9000
tcgttccact gagcgtcaga ccccgtagaa aagatcaaag gatcttcttg agatcctttt      9060
tttctgcgcg taatctgctg cttgcaaaca aaaaaaccac cgctaccagc ggtggtttgt      9120
ttgccggatc aagagctacc aactcttttt ccgaaggtaa ctggcttcag cagagcgcag      9180
ataccaaata ctgtccttct agtgtagccg tagttaggcc accacttcaa gaactctgta      9240
gcaccgccta catacctcgc tctgctaatc ctgttaccag tggctgctgc cagtggcgat      9300
aagtcgtgtc ttaccgggtt ggactcaaga cgatagttac cggataaggc gcagcggtcg      9360
ggctgaacgg ggggttcgtg cacacagccc agcttggagc gaacgaccta caccgaactg      9420
agatacctac agcgtgagct atgagaaagc gccacgcttc ccgaagggag aaaggcggac      9480
aggtatccgg taagcggcag ggtcggaaca ggagagcgca cgagggagct tccaggggga      9540
aacgcctggt atctttatag tcctgtcggg tttcgccacc tctgacttga gcgtcgattt      9600
ttgtgatgct cgtcaggggg gcggagccta tggaaaaacg ccagcaacgc ggccttttta      9660
cggttcctgg ccttttgctg gccttttgct cacatgttct ttcctgcgtt atcccctgat      9720
tctgtggat                                                              9729
```

<210> SEQ ID NO 14
<211> LENGTH: 124
<212> TYPE: PRT
<213> ORGANISM: Homo sapiens

<400> SEQUENCE: 14

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45
```

```
Ala Arg Ile Tyr Pro Thr Asn Gly Tyr Thr Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys
        115                 120

<210> SEQ ID NO 15
<211> LENGTH: 372
<212> TYPE: DNA
<213> ORGANISM: Homo sapiens

<400> SEQUENCE: 15
gaggtgcagc tcgtggagag tggtggcggg ttggtccagc caggcgggtc tctgcgattg      60
agctgtgctg cctctggatt taacatcaaa gacacgtaca tccattgggt gagacaggcc    120
cccggcaagg gccttgaatg ggtagctaga atctatccca ctaacggcta caccagatac    180
gctgatagcg ttaaaggaag gtttactatt tctgccgaca cctccaagaa taccgcatat    240
ctacagatga actccctgcg cgctgaggac accgctgtgt attactgctc acgttggggg    300
ggagacggat tctacgcaat ggactactgg ggccagggta ccttagtgac agttagcagt    360
gcctctacta ag                                                        372

<210> SEQ ID NO 16
<211> LENGTH: 108
<212> TYPE: DNA
<213> ORGANISM: artificial
<220> FEATURE:
<223> OTHER INFORMATION: synthetic oligo

<400> SEQUENCE: 16
gaggtgcagc tcgtggagag tggtggcggg ttggtccagc caggcgggtc tctgcgattg      60
agctgtgctg cctctggatt taacatcaaa gacacgtaca tccattgg                 108

<210> SEQ ID NO 17
<211> LENGTH: 105
<212> TYPE: DNA
<213> ORGANISM: artificial
<220> FEATURE:
<223> OTHER INFORMATION: synthetic oligo

<400> SEQUENCE: 17
tttaacgcta tcagcgtatc tggtgtagcc gttagtggga tagattctag ctacccattc      60
aaggcccttg ccgggggcct gtctcaccca atggatgtac gtgtc                    105

<210> SEQ ID NO 18
<211> LENGTH: 105
<212> TYPE: DNA
<213> ORGANISM: artificial
<220> FEATURE:
<223> OTHER INFORMATION: synthetic oligo

<400> SEQUENCE: 18
tacgctgata gcgttaaagg aaggtttact atttctgccg acacctccaa gaataccgca      60
tatctacaga tgaactccct gcgcgctgag gacaccgctg tgtat                    105
```

<210> SEQ ID NO 19
<211> LENGTH: 107
<212> TYPE: DNA
<213> ORGANISM: artificial
<220> FEATURE:
<223> OTHER INFORMATION: synthetic oligo

<400> SEQUENCE: 19

```
cttagtagag cactgctaac tgtcactaag gtaccctggc cccagtagtc cattgcgtag     60
aatccgtctc cccccaacg tgagcagtaa tacacagcgg tgtcctc                   107
```

<210> SEQ ID NO 20
<211> LENGTH: 30
<212> TYPE: DNA
<213> ORGANISM: artificial
<220> FEATURE:
<223> OTHER INFORMATION: synthetic oligo

<400> SEQUENCE: 20

```
gccaagcttg aggtgcagct cgtggagagt                                      30
```

<210> SEQ ID NO 21
<211> LENGTH: 30
<212> TYPE: DNA
<213> ORGANISM: artificial
<220> FEATURE:
<223> OTHER INFORMATION: synthetic oligo

<400> SEQUENCE: 21

```
aggggggccct tagtagaggc actgctaact                                     30
```

<210> SEQ ID NO 22
<211> LENGTH: 107
<212> TYPE: PRT
<213> ORGANISM: Homo sapiens

<400> SEQUENCE: 22

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

<210> SEQ ID NO 23
<211> LENGTH: 321
<212> TYPE: DNA
<213> ORGANISM: Homo sapiens

<400> SEQUENCE: 23

```
gatatacaga tgacacagtc tccgtcaagt ctgagcgcaa gcgtgggcga ccgggtaaca     60
attacctgta gagccagcca ggacgtaaat acagccgtgg cctggtatca gcaaaaacct   120
ggtaaagctc ctaagcttct gatctactct gcctcgttcc tttatagcgg ggtgccaagc   180
```

```
cgcttctccg gatctaggtc tggaacagac tttactctga ccatttccag tctccagccc    240
gaagactttg ctacctacta ttgccagcaa cattacacga ctccacccac atttgggcag    300
ggcaccaagg tcgagatcaa g                                              321
```

<210> SEQ ID NO 24
<211> LENGTH: 93
<212> TYPE: DNA
<213> ORGANISM: artificial
<220> FEATURE:
<223> OTHER INFORMATION: synthetic oligo

<400> SEQUENCE: 24

```
gatatacaga tgacacagtc tccgtcaagt ctgagcgcaa gcgtgggcga ccgggtaaca    60
attacctgta gagccagcca ggacgtaaat aca                                 93
```

<210> SEQ ID NO 25
<211> LENGTH: 95
<212> TYPE: DNA
<213> ORGANISM: artificial
<220> FEATURE:
<223> OTHER INFORMATION: synthetic oligo

<400> SEQUENCE: 25

```
ccgctataaa ggaacgaggc agagtagatc agaagcttag gagctttacc aggttttgc     60 tgataccagg ccacggctgt atttacgtcc tggct                               95
```

<210> SEQ ID NO 26
<211> LENGTH: 94
<212> TYPE: DNA
<213> ORGANISM: artificial
<220> FEATURE:
<223> OTHER INFORMATION: synthetic oligo

<400> SEQUENCE: 26

```
ctcgttcctt tatagcgggg tgccaagccg cttctccgga tctaggtctg aacagactt     60 tactctgacc atttccagtc tccagcccga agac                                94
```

<210> SEQ ID NO 27
<211> LENGTH: 93
<212> TYPE: DNA
<213> ORGANISM: artificial
<220> FEATURE:
<223> OTHER INFORMATION: synthetic oligo

<400> SEQUENCE: 27

```
cttgatctcg accttggtgc cctgcccaaa tgtgggtgga gtcgtgtaat gttgctggca    60
atagtaggta gcaaagtctt cgggctggag act                                 93
```

<210> SEQ ID NO 28
<211> LENGTH: 30
<212> TYPE: DNA
<213> ORGANISM: artificial
<220> FEATURE:
<223> OTHER INFORMATION: synthetic oligo

<400> SEQUENCE: 28

```
gccaagcttg atatacagat gacacagtct                                     30
```

<210> SEQ ID NO 29
<211> LENGTH: 30
<212> TYPE: DNA
<213> ORGANISM: artificial

-continued

```
<220> FEATURE:
<223> OTHER INFORMATION: synthetic oligo

<400> SEQUENCE: 29
cgcggattcc ttgatctcga ccttggtgcc                                          30
```